US009028441B2

(12) United States Patent
Kuhn

(10) Patent No.: US 9,028,441 B2
(45) Date of Patent: May 12, 2015

(54) APPARATUS AND METHOD USED WITH GUIDANCE SYSTEM FOR FEEDING AND SUCTIONING

(75) Inventor: Thomas Kuhn, Buffalo Grove, IL (US)

(73) Assignee: Corpak Medsystems, Inc., Buffalo Grove, IL (US)

( * ) Notice: Subject to any disclaimer, the term of this patent is extended or adjusted under 35 U.S.C. 154(b) by 80 days.

(21) Appl. No.: 13/606,977

(22) Filed: Sep. 7, 2012

(65) Prior Publication Data

US 2013/0245542 A1 Sep. 19, 2013

Related U.S. Application Data

(60) Provisional application No. 61/532,187, filed on Sep. 8, 2011.

(51) Int. Cl.
*A61J 15/00* (2006.01)

(52) U.S. Cl.
CPC .......... *A61J 15/0096* (2013.01); *A61J 15/0003* (2013.01); *A61J 15/0069* (2013.01); *A61J 2200/76* (2013.01); *A61J 2205/00* (2013.01); *A61J 2015/0088* (2013.01)

(58) Field of Classification Search
CPC ... A61J 15/00; A61J 15/0003; A61J 15/0015; A61J 15/0023; A61J 15/0069; A61J 15/0096; A61M 2039/085; A61M 2202/0482; A61M 2001/1008
USPC ........ 604/43, 533, 284, 541, 909–910; 600/9, 600/12
See application file for complete search history.

(56) References Cited

U.S. PATENT DOCUMENTS

| 803,469 A | 10/1905 | Cilley et al. |
|---|---|---|
| 910,125 A | 1/1909 | Graser |
| 921,368 A | 5/1909 | Crook |
| 1,074,706 A | 10/1913 | Ferguson |
| 1,211,928 A | 1/1917 | Fisher |
| 1,242,174 A | 10/1917 | Gouch |
| 1,335,672 A | 3/1920 | DuNouy |
| 1,380,991 A | 6/1921 | Collins |

(Continued)

FOREIGN PATENT DOCUMENTS

| AU | 1989PJ04337 | 5/1989 |
|---|---|---|
| AU | 642647 | 10/1993 |

(Continued)

OTHER PUBLICATIONS

International Search Report and Written Opinion issued on Dec. 12, 2012 for corresponding International Appln. No. PCT/US2012/054172.

(Continued)

*Primary Examiner* — Quynh-Nhu H Vu
(74) *Attorney, Agent, or Firm* — K&L Gates LLP

(57) ABSTRACT

In one example embodiment, the tube assembly is configured to be used in conjunction with a tube assembly guidance system. The tube assembly includes a first connector, a feeding tube connected to the first connector, a second connector connected to the feeding tube, and a suctioning tube connected to the second connector. The suctioning tube is configured to receive the feeding tube. The feeding tube is configured to allow enteral feeding while the suctioning tube is configured to allow suctioning or decompression of a patient's stomach.

5 Claims, 8 Drawing Sheets

(56) References Cited

U.S. PATENT DOCUMENTS

| | | |
|---|---|---|
| 1,417,141 A | 5/1922 | Carter |
| 1,615,873 A | 2/1927 | Fitch |
| 1,635,373 A | 7/1927 | Lofholm |
| 1,696,763 A | 12/1928 | Hare |
| 1,736,182 A | 11/1929 | Wilkins |
| 1,767,073 A | 6/1930 | Ingold |
| 1,865,926 A | 7/1932 | Laing |
| 1,879,249 A | 9/1932 | Honsaker |
| 1,888,349 A | 11/1932 | Jacoby |
| 1,899,781 A | 2/1933 | Twiss |
| 1,903,681 A | 4/1933 | Merliss |
| 2,103,050 A | 12/1937 | White |
| 2,116,083 A | 5/1938 | Rusch |
| 2,218,285 A | 10/1940 | Jellik, Jr. |
| 2,321,355 A | 1/1942 | Berman |
| 2,409,343 A | 10/1946 | Curtis |
| 2,491,516 A | 12/1949 | Piggot et al. |
| 2,521,745 A | 9/1950 | Pope |
| 2,626,855 A | 1/1953 | Hand |
| 2,671,028 A | 3/1954 | Clark |
| 2,694,984 A | 11/1954 | Daniels |
| 2,699,167 A | 1/1955 | Raiche |
| 2,717,598 A | 9/1955 | Krasno |
| 2,731,053 A | 1/1956 | Lockhart |
| 2,735,432 A | 2/1956 | Hudson |
| 2,816,692 A | 12/1957 | Schade |
| 2,817,372 A | 12/1957 | Barr, Sr. et al. |
| 2,820,959 A | 1/1958 | Bell |
| 2,863,458 A | 12/1958 | Modny et al. |
| 2,906,944 A | 9/1959 | Lebourg |
| 2,908,863 A | 10/1959 | Neff |
| 2,935,067 A | 5/1960 | Bouet |
| 2,941,822 A | 6/1960 | Moecker |
| 2,949,910 A | 8/1960 | Brown et al. |
| 2,957,196 A | 10/1960 | Kreider et al. |
| 2,961,691 A | 11/1960 | Roy et al. |
| 2,969,063 A | 1/1961 | Broman |
| 2,986,142 A | 5/1961 | Bieberdorf et al. |
| 2,999,387 A | 9/1961 | Andelin |
| 3,001,525 A | 9/1961 | Hendricks |
| 3,042,030 A | 7/1962 | Read |
| 3,043,309 A | 7/1962 | McCarthy |
| 3,067,015 A | 12/1962 | Lawdermilt |
| 3,087,493 A | 4/1963 | Schossow |
| 3,090,532 A | 5/1963 | Robson |
| 3,092,106 A | 6/1963 | Butler |
| D196,611 S | 10/1963 | Alder et al. |
| 3,108,717 A | 10/1963 | Kindseth |
| 3,189,031 A | 6/1965 | Andersen |
| 3,190,290 A | 6/1965 | Alley et al. |
| 3,190,291 A | 6/1965 | Foley |
| 3,229,678 A | 1/1966 | Anspach |
| 3,230,767 A | 1/1966 | Heigl et al. |
| 3,239,096 A | 3/1966 | Buono et al. |
| 3,239,104 A | 3/1966 | Scholle |
| 3,241,554 A | 3/1966 | Coanda |
| 3,253,588 A | 5/1966 | Vuilleumier et al. |
| 3,253,594 A | 5/1966 | Matthews et al. |
| 3,288,332 A | 11/1966 | Etter et al. |
| 3,311,267 A | 3/1967 | Lee et al. |
| 3,311,268 A | 3/1967 | Fields |
| 3,346,464 A | 10/1967 | Ernst |
| 3,373,735 A | 3/1968 | Gallagher |
| 3,395,710 A | 8/1968 | Stratton et al. |
| 3,395,711 A | 8/1968 | Pizak, Jr. |
| 3,452,742 A | 7/1969 | Muller |
| 3,471,773 A | 10/1969 | Penland |
| 3,528,869 A | 9/1970 | Dereniuk |
| 3,539,674 A | 11/1970 | Dereniuk et al. |
| 3,547,103 A | 12/1970 | Cook |
| 3,548,805 A | 12/1970 | Datsenko et al. |
| 3,556,294 A | 1/1971 | Walck, III et al. |
| 3,568,679 A | 3/1971 | Reif |
| 3,593,713 A | 7/1971 | Bogoff |
| 3,597,124 A | 8/1971 | Adams |
| 3,597,680 A | 8/1971 | Haddon |
| 3,605,750 A | 9/1971 | Sheridan et al. |
| 3,617,865 A | 11/1971 | Hakata |
| 3,618,614 A | 11/1971 | Flynn |
| 3,622,784 A | 11/1971 | Del Guercio |
| 3,623,101 A | 11/1971 | Grebe et al. |
| 3,625,200 A | 12/1971 | Muller |
| 3,640,282 A | 2/1972 | Kamen et al. |
| 3,645,562 A | 2/1972 | Fandetti et al. |
| 3,648,703 A | 3/1972 | Manker |
| 3,653,050 A | 3/1972 | Eggleston, Jr. |
| 3,656,161 A | 4/1972 | MacPherson |
| 3,656,485 A | 4/1972 | Robertson |
| 3,659,588 A | 5/1972 | Kahn et al. |
| 3,661,148 A | 5/1972 | Kolin |
| 3,664,339 A | 5/1972 | Santomieri |
| 3,667,781 A | 6/1972 | Holbrook |
| 3,683,911 A | 8/1972 | McCormick |
| 3,709,211 A | 1/1973 | Hawkins |
| 3,731,684 A | 5/1973 | Spiegel |
| 3,749,086 A | 7/1973 | Kline et al. |
| 3,749,134 A | 7/1973 | Slinghluff et al. |
| 3,771,527 A | 11/1973 | Ruisi |
| 3,782,388 A | 1/1974 | Page |
| 3,794,041 A | 2/1974 | Frei et al. |
| 3,799,173 A | 3/1974 | Kamen |
| 3,826,396 A | 7/1974 | Frassica |
| 3,831,086 A | 8/1974 | Pesto |
| 3,831,587 A | 8/1974 | Boyd |
| 3,856,020 A | 12/1974 | Kovac |
| 3,873,814 A | 3/1975 | Mirdadian |
| 3,880,311 A | 4/1975 | McPhee |
| 3,881,254 A | 5/1975 | Epstein |
| 3,889,685 A | 6/1975 | Miller, Jr. et al. |
| 3,902,932 A | 9/1975 | Gdanski et al. |
| 3,915,212 A | 10/1975 | Bujan et al. |
| 3,929,126 A | 12/1975 | Corsaut |
| 3,932,805 A | 1/1976 | Abe et al. |
| 3,985,135 A | 10/1976 | Carpenter |
| 4,007,740 A | 2/1977 | Owen |
| 4,020,829 A | 5/1977 | Willson et al. |
| 4,025,241 A | 5/1977 | Clemens |
| 4,027,659 A | 6/1977 | Slingluff |
| 4,057,065 A | 11/1977 | Thow |
| 4,058,121 A | 11/1977 | Choksi et al. |
| 4,072,146 A | 2/1978 | Howes |
| 4,076,285 A | 2/1978 | Martinez |
| 4,085,866 A | 4/1978 | Fekl |
| 4,114,625 A | 9/1978 | Onat |
| 4,141,364 A | 2/1979 | Schultze |
| 4,148,319 A | 4/1979 | Kasper et al. |
| 4,173,228 A | 11/1979 | Van Steenwyk et al. |
| 4,176,662 A | 12/1979 | Frazer |
| 4,185,948 A | 1/1980 | Maguire |
| 4,187,893 A | 2/1980 | BuJan |
| 4,198,971 A | 4/1980 | Noiles |
| 4,201,208 A | 5/1980 | Cambio, Jr. |
| 4,211,519 A | 7/1980 | Hogan |
| 4,220,813 A | 9/1980 | Kyle |
| 4,220,814 A | 9/1980 | Kyle et al. |
| 4,229,299 A | 10/1980 | Savitz et al. |
| 4,230,123 A | 10/1980 | Hawkins, Jr. |
| 4,232,421 A | 11/1980 | Tucker |
| 4,256,437 A | 3/1981 | Brown |
| 4,257,416 A | 3/1981 | Prager |
| 4,257,421 A | 3/1981 | Beal |
| 4,257,748 A | 3/1981 | Ives et al. |
| 4,259,952 A | 4/1981 | Avoy |
| 4,261,363 A | 4/1981 | Russo |
| 4,269,332 A | 5/1981 | Conn |
| 4,270,542 A | 6/1981 | Plumley |
| 4,278,085 A | 7/1981 | Shim |
| 4,282,863 A | 8/1981 | Beigler et al. |
| 4,288,205 A | 9/1981 | Henk |
| 4,296,949 A | 10/1981 | Muetterties et al. |
| 4,298,045 A | 11/1981 | Weiler et al. |
| 4,311,140 A | 1/1982 | Bridgman |
| 4,315,513 A | 2/1982 | Nawash et al. |
| 4,317,078 A | 2/1982 | Weed et al. |

(56) References Cited

U.S. PATENT DOCUMENTS

| | | | |
|---|---|---|---|
| 4,323,065 A | 4/1982 | King |
| 4,344,434 A | 8/1982 | Robertson |
| 4,346,703 A | 8/1982 | Dennehey et al. |
| 4,349,024 A | 9/1982 | Raiston, Jr. |
| 4,352,951 A | 10/1982 | Kyle |
| 4,354,492 A | 10/1982 | McPhee |
| 4,356,824 A | 11/1982 | Vazquez |
| 4,363,320 A | 12/1982 | Kossove |
| 4,364,394 A | 12/1982 | Wilkinson |
| 4,379,261 A | 4/1983 | Lakin |
| 4,381,011 A | 4/1983 | Somers, III |
| 4,388,076 A | 6/1983 | Waters |
| 4,390,017 A | 6/1983 | Harrison et al. |
| 4,392,853 A | 7/1983 | Muto |
| 4,392,855 A | 7/1983 | Oreopoulos |
| 4,393,873 A | 7/1983 | Nawash et al. |
| 4,396,382 A * | 8/1983 | Goldhaber ................ 604/28 |
| 4,405,316 A | 9/1983 | Mittleman |
| 4,410,320 A | 10/1983 | Dykstra |
| 4,411,656 A | 10/1983 | Cornett, III |
| 4,411,661 A | 10/1983 | Kersten |
| 4,416,289 A | 11/1983 | Bresler |
| 4,419,094 A | 12/1983 | Patel |
| 4,424,833 A | 1/1984 | Spector et al. |
| 4,432,763 A | 2/1984 | Manschot et al. |
| 4,435,174 A | 3/1984 | Redmond et al. |
| 4,439,188 A | 3/1984 | Dennehey et al. |
| 4,445,089 A | 4/1984 | Codrington |
| 4,449,974 A | 5/1984 | Messingschlager |
| 4,464,175 A | 8/1984 | Altman et al. |
| 4,472,116 A | 9/1984 | Wenstrup |
| 4,473,094 A | 9/1984 | Harris |
| 4,479,274 A | 10/1984 | Biby |
| 4,484,916 A | 11/1984 | McPhee |
| 4,487,604 A | 12/1984 | Iwatschenko et al. |
| 4,490,143 A | 12/1984 | Quinn et al. |
| 4,496,295 A | 1/1985 | King |
| 4,496,347 A | 1/1985 | MacLean et al. |
| 4,498,843 A | 2/1985 | Schneider et al. |
| 4,515,584 A | 5/1985 | Abe et al. |
| 4,516,968 A | 5/1985 | Marshall et al. |
| 4,516,970 A | 5/1985 | Kaufman et al. |
| 4,518,327 A | 5/1985 | Hackman |
| 4,521,212 A | 6/1985 | Ruschke |
| 4,529,102 A | 7/1985 | Quinn et al. |
| 4,531,943 A | 7/1985 | Van Tassel et al. |
| 4,538,836 A | 9/1985 | Krutten |
| 4,543,089 A | 9/1985 | Moss |
| 4,549,879 A | 10/1985 | Groshong et al. |
| 4,552,554 A | 11/1985 | Gould et al. |
| 4,553,971 A | 11/1985 | Ashley et al. |
| 4,557,261 A | 12/1985 | Rugheimer |
| 4,559,046 A | 12/1985 | Groshong et al. |
| 4,568,338 A | 2/1986 | Todd |
| 4,569,675 A | 2/1986 | Prosl et al. |
| 4,572,198 A | 2/1986 | Codrington |
| 4,573,576 A | 3/1986 | Krol |
| 4,574,173 A | 3/1986 | Bennett |
| 4,580,573 A | 4/1986 | Quinn |
| D284,035 S | 5/1986 | DeLeeuwe et al. |
| 4,588,396 A | 5/1986 | Stroebel et al. |
| 4,588,402 A | 5/1986 | Igari et al. |
| 4,594,074 A | 6/1986 | Andersen et al. |
| 4,598,699 A | 7/1986 | Garen et al. |
| 4,607,868 A | 8/1986 | Harvey et al. |
| 4,610,673 A | 9/1986 | Russo |
| 4,613,323 A | 9/1986 | Andersen et al. |
| 4,636,144 A | 1/1987 | Abe et al. |
| 4,639,019 A | 1/1987 | Mittleman |
| 4,642,092 A | 2/1987 | Moss |
| 4,645,492 A | 2/1987 | Weeks |
| 4,654,036 A | 3/1987 | Tolkoff |
| 4,655,763 A | 4/1987 | Malcolm et al. |
| 4,658,834 A | 4/1987 | Blankenship et al. |
| 4,666,433 A | 5/1987 | Parks |
| 4,668,222 A | 5/1987 | Poirier |
| 4,668,225 A | 5/1987 | Russo |
| 4,671,796 A | 6/1987 | Groshong et al. |
| 4,672,972 A | 6/1987 | Berke |
| 4,673,334 A | 6/1987 | Allington et al. |
| 4,676,782 A | 6/1987 | Yamamoto et al. |
| 4,681,564 A | 7/1987 | Landreneau |
| 4,683,916 A | 8/1987 | Raines |
| 4,684,038 A | 8/1987 | Gaul et al. |
| 4,685,901 A | 8/1987 | Parks |
| 4,685,912 A | 8/1987 | Jones |
| 4,687,470 A | 8/1987 | Okada |
| 4,687,471 A | 8/1987 | Twardowski et al. |
| 4,690,138 A | 9/1987 | Heyden |
| 4,692,152 A | 9/1987 | Emde |
| 4,699,296 A | 10/1987 | Schrock, Jr. |
| 4,701,159 A | 10/1987 | Brown et al. |
| 4,701,162 A | 10/1987 | Rosenberg |
| 4,701,163 A | 10/1987 | Parks |
| 4,701,166 A | 10/1987 | Groshong et al. |
| 4,714,460 A | 12/1987 | Calderon |
| 4,717,385 A | 1/1988 | Cameron |
| 4,719,924 A | 1/1988 | Crittenden et al. |
| 4,721,115 A | 1/1988 | Owens |
| 4,722,344 A | 2/1988 | Cambron et al. |
| 4,735,607 A | 4/1988 | Keith, Jr. |
| 4,743,231 A | 5/1988 | Kay et al. |
| 4,744,366 A | 5/1988 | Jang |
| 4,753,639 A | 6/1988 | Iwatschenko |
| 4,753,640 A | 6/1988 | Nichols et al. |
| 4,758,219 A | 7/1988 | Sacks |
| 4,762,519 A | 8/1988 | Frimberger |
| 4,763,667 A | 8/1988 | Manzo |
| 4,769,014 A | 9/1988 | Russo |
| 4,772,269 A | 9/1988 | Twardowski et al. |
| 4,773,901 A | 9/1988 | Norton |
| 4,774,940 A | 10/1988 | Linder |
| 4,778,455 A | 10/1988 | Kousai et al. |
| 4,778,477 A | 10/1988 | Lauchenauer |
| 4,779,611 A | 10/1988 | Grooters et al. |
| 4,781,704 A | 11/1988 | Potter |
| 4,787,890 A | 11/1988 | Ufermann |
| 4,795,430 A | 1/1989 | Quinn et al. |
| 4,795,434 A | 1/1989 | Kujawski |
| 4,795,446 A | 1/1989 | Fecht |
| 4,798,593 A | 1/1989 | Iwatschenko |
| 4,798,605 A | 1/1989 | Steiner et al. |
| 4,809,713 A | 3/1989 | Grayzel |
| 4,811,737 A | 3/1989 | Rydell |
| 4,820,270 A | 4/1989 | Hardcastie et al. |
| 4,820,288 A | 4/1989 | Isono |
| 4,822,338 A | 4/1989 | Longmore et al. |
| 4,823,805 A | 4/1989 | Wojcik |
| 4,824,435 A | 4/1989 | Giesy et al. |
| 4,826,481 A | 5/1989 | Sacks et al. |
| 4,828,550 A * | 5/1989 | Kurimoto ................ 604/171 |
| 4,832,584 A | 5/1989 | Nassif |
| 4,834,712 A | 5/1989 | Quinn et al. |
| 4,834,713 A | 5/1989 | Suthanthiran |
| 4,834,732 A | 5/1989 | Steer et al. |
| 4,838,881 A | 6/1989 | Bennett |
| 4,854,330 A | 8/1989 | Evans, III et al. |
| 4,860,742 A | 8/1989 | Park et al. |
| 4,863,424 A | 9/1989 | Blake et al. |
| 4,863,438 A | 9/1989 | Gauderer et al. |
| 4,863,442 A | 9/1989 | DeMello et al. |
| 4,867,742 A | 9/1989 | Calderon |
| 4,884,013 A | 11/1989 | Jackson et al. |
| 4,886,067 A | 12/1989 | Palermo |
| 4,895,275 A | 1/1990 | Quinn et al. |
| 4,900,306 A | 2/1990 | Quinn et al. |
| 4,904,238 A | 2/1990 | Williams |
| 4,905,698 A | 3/1990 | Strohl, Jr. et al. |
| 4,913,703 A | 4/1990 | Pasqualucci et al. |
| 4,921,138 A | 5/1990 | Quinn et al. |
| 4,923,061 A | 5/1990 | Trombley, III |
| 4,929,236 A | 5/1990 | Sampson |
| 4,935,004 A | 6/1990 | Cruz |
| 4,943,275 A | 7/1990 | Stricker |

(56) References Cited

U.S. PATENT DOCUMENTS

| | | | |
|---|---|---|---|
| 4,944,732 | A | 7/1990 | Russo |
| 4,946,440 | A | 8/1990 | Hall |
| 4,950,254 | A | 8/1990 | Andersen et al. |
| 4,958,634 | A | 9/1990 | Jang |
| 4,959,055 | A | 9/1990 | Hillyer |
| 4,961,430 | A | 10/1990 | Sheahon |
| 4,963,132 | A | 10/1990 | Gibson |
| 4,963,133 | A | 10/1990 | Whipple |
| 4,966,583 | A | 10/1990 | Debbas |
| 4,969,879 | A | 11/1990 | Lichte |
| 4,973,329 | A | 11/1990 | Park et al. |
| 4,976,691 | A | 12/1990 | Sahota |
| 4,976,703 | A | 12/1990 | Franetzki et al. |
| 4,981,482 | A | 1/1991 | Ichikawa |
| 4,986,807 | A | 1/1991 | Farr |
| 4,990,139 | A | 2/1991 | Jang |
| 4,991,629 | A | 2/1991 | Ernesto et al. |
| 4,994,033 | A | 2/1991 | Shockey et al. |
| 4,994,048 | A | 2/1991 | Metzger |
| 4,995,863 | A | 2/1991 | Nichols et al. |
| 5,005,592 | A | 4/1991 | Cartmell |
| 5,007,900 | A | 4/1991 | Picha et al. |
| 5,014,008 | A | 5/1991 | Flowerden |
| 5,017,192 | A | 5/1991 | Dodge et al. |
| 5,017,199 | A | 5/1991 | Marten et al. |
| 5,026,352 | A | 6/1991 | Anderson |
| 5,037,387 | A | 8/1991 | Quinn et al. |
| 5,040,543 | A | 8/1991 | Badera et al. |
| 5,041,085 | A | 8/1991 | Osborne et al. |
| 5,042,486 | A | 8/1991 | Pfeiler et al. |
| 5,044,369 | A | 9/1991 | Sahota |
| 5,045,071 | A | 9/1991 | McCormick et al. |
| 5,047,021 | A | 9/1991 | Utterberg |
| 5,049,139 | A | 9/1991 | Gilchrist |
| 5,053,004 | A | 10/1991 | Markel et al. |
| 5,057,091 | A | 10/1991 | Andersen |
| 5,057,093 | A | 10/1991 | Clegg et al. |
| 5,059,170 | A | 10/1991 | Cameron |
| 5,059,178 | A | 10/1991 | Ya |
| 5,061,256 | A | 10/1991 | Wampler |
| 5,073,166 | A | 12/1991 | Parks et al. |
| 5,074,846 | A | 12/1991 | Clegg et al. |
| 5,077,352 | A | 12/1991 | Elton |
| 5,078,681 | A | 1/1992 | Kawashima |
| 5,078,743 | A | 1/1992 | Mikalov et al. |
| D324,566 | S | 3/1992 | Schmidt et al. |
| 5,092,847 | A | 3/1992 | Pozzo |
| 5,092,850 | A | 3/1992 | Buma |
| 5,098,378 | A | 3/1992 | Piontek et al. |
| 5,098,405 | A | 3/1992 | Peterson et al. |
| 5,099,845 | A | 3/1992 | Besz et al. |
| 5,104,157 | A | 4/1992 | Bahner |
| 5,108,368 | A | 4/1992 | Hammerslag et al. |
| 5,112,310 | A | 5/1992 | Grobe |
| 5,125,897 | A | 6/1992 | Quinn et al. |
| 5,125,915 | A | 6/1992 | Berry et al. |
| 5,131,407 | A | 7/1992 | Ischinger et al. |
| 5,147,308 | A | 9/1992 | Singer |
| 5,147,315 | A | 9/1992 | Weber |
| 5,147,332 | A | 9/1992 | Moorehead |
| 5,149,330 | A | 9/1992 | Brightbill |
| 5,151,086 | A | 9/1992 | Duh et al. |
| 5,152,749 | A | 10/1992 | Giesy et al. |
| 5,152,756 | A | 10/1992 | Quinn et al. |
| 5,156,596 | A | 10/1992 | Balbierz et al. |
| 5,160,325 | A | 11/1992 | Nichols et al. |
| 5,167,627 | A | 12/1992 | Glegg et al. |
| 5,167,635 | A | 12/1992 | Haber et al. |
| 5,171,216 | A | 12/1992 | Dasse et al. |
| 5,179,174 | A | 1/1993 | Elton |
| 5,183,045 | A | 2/1993 | Takamura et al. |
| 5,196,796 | A | 3/1993 | Misic et al. |
| 5,207,648 | A | 5/1993 | Gross |
| 5,211,165 | A | 5/1993 | Dumoulin et al. |
| 5,217,440 | A | 6/1993 | Frassica |
| 5,224,933 | A | 7/1993 | Bromander |
| 5,226,423 | A | 7/1993 | Tenerz et al. |
| D338,726 | S | 8/1993 | Andersen et al. |
| 5,231,989 | A | 8/1993 | Middleman et al. |
| 5,231,994 | A | 8/1993 | Harmjanz |
| 5,234,417 | A | 8/1993 | Parks et al. |
| 5,250,040 | A | 10/1993 | Parks et al. |
| 5,251,027 | A | 10/1993 | LaBeau |
| 5,251,635 | A | 10/1993 | Dumoulin et al. |
| 5,253,647 | A | 10/1993 | Takahasi et al. |
| 5,255,680 | A | 10/1993 | Darrow et al. |
| 5,257,636 | A | 11/1993 | White |
| 5,263,944 | A | 11/1993 | Vidal et al. |
| 5,265,610 | A | 11/1993 | Darrow et al. |
| 5,265,622 | A | 11/1993 | Barbere |
| 5,267,968 | A | 12/1993 | Russo |
| 5,267,969 | A | 12/1993 | Hirsch et al. |
| 5,267,970 | A | 12/1993 | Chin et al. |
| 5,273,025 | A | 12/1993 | Sakiyama et al. |
| 5,279,607 | A | 1/1994 | Schentag et al. |
| 5,284,474 | A | 2/1994 | Adair |
| 5,290,282 | A | 3/1994 | Casscells |
| 5,290,585 | A | 3/1994 | Elton |
| 5,300,044 | A | 4/1994 | Classey et al. |
| 5,303,714 | A | 4/1994 | Abele et al. |
| 5,305,742 | A | 4/1994 | Styers et al. |
| 5,308,325 | A | 5/1994 | Quinn et al. |
| 5,318,543 | A | 6/1994 | Ross et al. |
| 5,325,873 | A | 7/1994 | Hirschi et al. |
| 5,334,153 | A | 8/1994 | McIntyre et al. |
| 5,336,203 | A | 8/1994 | Goldhardt et al. |
| 5,342,321 | A | 8/1994 | Potter |
| 5,352,795 | A | 10/1994 | Souza et al. |
| 5,353,795 | A | 10/1994 | Souza et al. |
| 5,353,807 | A | 10/1994 | DeMarco |
| 5,356,382 | A | 10/1994 | Picha et al. |
| 5,356,391 | A | 10/1994 | Stewart |
| 5,365,942 | A | 11/1994 | Shank |
| 5,372,592 | A | 12/1994 | Gambale |
| 5,374,251 | A | 12/1994 | Smith |
| 5,374,254 | A | 12/1994 | Buma |
| 5,375,596 | A | 12/1994 | Twiss et al. |
| 5,377,678 | A | 1/1995 | Dumoulin et al. |
| 5,385,561 | A | 1/1995 | Cemy |
| 5,386,828 | A | 2/1995 | Owens et al. |
| 5,389,091 | A | 2/1995 | Moorehead |
| 5,391,152 | A | 2/1995 | Patterson |
| 5,391,159 | A | 2/1995 | Hirsch et al. |
| 5,391,199 | A | 2/1995 | Ben-Haim |
| 5,395,366 | A | 3/1995 | D'Andrea et al. |
| 5,399,173 | A | 3/1995 | Parks et al. |
| 5,409,459 | A | 4/1995 | Gambale |
| 5,417,664 | A | 5/1995 | Felix et al. |
| 5,421,819 | A | 6/1995 | Edwards et al. |
| 5,423,764 | A | 6/1995 | Fry |
| 5,425,367 | A | 6/1995 | Shapiro et al. |
| 5,429,132 | A | 7/1995 | Guy et al. |
| 5,431,640 | A | 7/1995 | Gabriel |
| 5,433,722 | A | 7/1995 | Sharpe et al. |
| 5,437,277 | A | 8/1995 | Dumoulin et al. |
| 5,443,066 | A | 8/1995 | Dumoulin et al. |
| 5,443,489 | A | 8/1995 | Ben-Haim |
| 5,445,150 | A | 8/1995 | Dumoulin et al. |
| 5,451,212 | A | 9/1995 | Andersen |
| 5,451,216 | A | 9/1995 | Quinn |
| 5,453,235 | A | 9/1995 | Calcote et al. |
| 5,458,583 | A | 10/1995 | McNeely et al. |
| 5,462,527 | A | 10/1995 | Stevens-Wright et al. |
| 5,480,422 | A | 1/1996 | Ben-Haim |
| 5,484,420 | A | 1/1996 | Russo |
| 5,489,249 | A | 2/1996 | Brewer et al. |
| 5,489,275 | A | 2/1996 | Thompson et al. |
| 5,492,119 | A | 2/1996 | Abrams |
| 5,498,249 | A | 3/1996 | Quinn |
| 5,512,037 | A | 4/1996 | Russell et al. |
| 5,545,141 | A | 8/1996 | Eld |
| 5,546,951 | A | 8/1996 | Ben-Haim |
| 5,555,898 | A | 9/1996 | Suzuki et al. |
| 5,556,385 | A | 9/1996 | Andersen |

(56) References Cited

U.S. PATENT DOCUMENTS

| | | | |
|---|---|---|---|
| 5,558,091 A | 9/1996 | Acker et al. |
| 5,571,093 A | 11/1996 | Cruz et al. |
| 5,571,116 A | 11/1996 | Bolanos et al. |
| 5,584,838 A | 12/1996 | Rona et al. |
| 5,592,939 A | 1/1997 | Martinelli |
| 5,599,322 A | 2/1997 | Quinn |
| 5,611,777 A | 3/1997 | Bowden et al. |
| 5,622,169 A | 4/1997 | Golden et al. |
| 5,624,413 A | 4/1997 | Markel et al. |
| 5,628,753 A | 5/1997 | Cracauer et al. |
| 5,630,794 A | 5/1997 | Lax et al. |
| 5,637,102 A | 6/1997 | Tolkoff et al. |
| 5,641,443 A | 6/1997 | Calcote et al. |
| 5,645,065 A | 7/1997 | Shapiro et al. |
| 5,649,974 A | 7/1997 | Nelson et al. |
| 5,650,759 A | 7/1997 | Hittman et al. |
| 5,658,253 A | 8/1997 | Piontek et al. |
| 5,665,064 A | 9/1997 | Bodicky et al. |
| 5,669,383 A | 9/1997 | Johnson |
| 5,676,674 A | 10/1997 | Bolanos et al. |
| 5,681,260 A | 10/1997 | Ueda et al. |
| RE35,648 E | 11/1997 | Tenerz et al. |
| 5,699,801 A | 12/1997 | Atalar et al. |
| 5,711,299 A | 1/1998 | Manwaring et al. |
| 5,713,946 A | 2/1998 | Ben-Haim |
| 5,715,817 A | 2/1998 | Stevens-Wright et al. |
| 5,716,347 A | 2/1998 | Gibbs et al. |
| 5,718,241 A | 2/1998 | Ben-Haim et al. |
| 5,718,678 A | 2/1998 | Fleming, III |
| 5,720,734 A | 2/1998 | Copenhaver et al. |
| 5,727,553 A | 3/1998 | Saad |
| 5,729,129 A | 3/1998 | Acker |
| 5,730,129 A | 3/1998 | Darrow et al. |
| 5,738,096 A | 4/1998 | Ben-Haim |
| 5,752,513 A | 5/1998 | Acker et al. |
| 5,762,064 A | 6/1998 | Polvani |
| 5,766,202 A | 6/1998 | Jones et al. |
| 5,769,843 A | 6/1998 | Abela et al. |
| 5,776,111 A | 7/1998 | Tesio |
| 5,779,669 A | 7/1998 | Haissaguerre et al. |
| 5,792,055 A | 8/1998 | McKinnon |
| 5,795,298 A | 8/1998 | Ben-Haim |
| 5,797,849 A | 8/1998 | Vesely et al. |
| 5,810,728 A | 9/1998 | Kuhn |
| 5,810,787 A | 9/1998 | Quinn |
| 5,810,789 A | 9/1998 | Powers et al. |
| 5,817,022 A | 10/1998 | Vesely |
| 5,827,202 A | 10/1998 | Miraki et al. |
| 5,830,144 A | 11/1998 | Vesely |
| 5,830,184 A | 11/1998 | Basta |
| 5,833,608 A | 11/1998 | Acker |
| 5,836,315 A | 11/1998 | Benderev et al. |
| 5,840,024 A | 11/1998 | Taniguchi et al. |
| 5,840,025 A | 11/1998 | Ben-Haim |
| 5,843,002 A | 12/1998 | Pecor et al. |
| 5,846,198 A | 12/1998 | Killmann |
| 5,851,195 A | 12/1998 | Gill |
| 5,860,952 A | 1/1999 | Quinn |
| 5,860,960 A | 1/1999 | Quinn |
| 5,865,816 A | 2/1999 | Quinn |
| 5,868,673 A | 2/1999 | Vesely |
| 5,868,674 A | 2/1999 | Glowinski et al. |
| 5,879,297 A | 3/1999 | Haynor et al. |
| 5,882,304 A | 3/1999 | Ehnholm et al. |
| 5,891,113 A | 4/1999 | Quinn |
| 5,897,562 A | 4/1999 | Bolanos et al. |
| 5,899,860 A | 5/1999 | Pfeiffer et al. |
| 5,902,238 A | 5/1999 | Golden et al. |
| 5,906,579 A | 5/1999 | Vander Salm et al. |
| 5,910,128 A | 6/1999 | Quinn |
| 5,913,820 A | 6/1999 | Bladen et al. |
| 5,916,162 A | 6/1999 | Snelten et al. |
| 5,931,811 A | 8/1999 | Halssaguerre et al. |
| 5,935,102 A | 8/1999 | Bowden et al. |
| 5,935,667 A | 8/1999 | Calcote et al. |
| 5,936,406 A | 8/1999 | Potthast |
| 5,938,603 A | 8/1999 | Ponzi |
| 5,941,855 A | 8/1999 | Picha et al. |
| 5,941,858 A | 8/1999 | Johnson |
| 5,944,023 A | 8/1999 | Johnson et al. |
| 5,944,732 A | 8/1999 | Raulerson et al. |
| 5,947,953 A | 9/1999 | Ash et al. |
| 5,951,472 A | 9/1999 | Van Vaals et al. |
| 5,954,665 A | 9/1999 | Ben-Haim |
| 5,964,757 A | 10/1999 | Ponzi |
| 5,989,231 A | 11/1999 | Snow et al. |
| 5,997,473 A | 12/1999 | Taniguchi et al. |
| 6,009,878 A | 1/2000 | Weijand et al. |
| 6,014,580 A | 1/2000 | Blume et al. |
| 6,016,439 A | 1/2000 | Acker |
| 6,019,725 A | 2/2000 | Vesely et al. |
| 6,019,727 A | 2/2000 | Koger et al. |
| 6,023,636 A | 2/2000 | Wendt et al. |
| 6,024,739 A | 2/2000 | Ponzi et al. |
| 6,030,364 A | 2/2000 | Durgin et al. |
| 6,033,382 A | 3/2000 | Basta |
| 6,036,673 A | 3/2000 | Quinn |
| 6,039,714 A | 3/2000 | Cracauer et al. |
| 6,047,214 A | 4/2000 | Mueller et al. |
| 6,052,610 A | 4/2000 | Koch |
| 6,059,718 A | 5/2000 | Taniguchi et al. |
| 6,064,905 A | 5/2000 | Webster et al. |
| 6,066,094 A | 5/2000 | Ben-Haim |
| 6,066,112 A | 5/2000 | Quinn |
| 6,073,043 A | 6/2000 | Schneider |
| 6,076,007 A | 6/2000 | England et al. |
| 6,077,243 A | 6/2000 | Quinn |
| 6,077,250 A | 6/2000 | Snow et al. |
| 6,082,361 A | 7/2000 | Morejon |
| 6,087,831 A | 7/2000 | Bornert et al. |
| 6,090,073 A | 7/2000 | Gill |
| 6,104,944 A | 8/2000 | Martinelli |
| 6,129,668 A | 10/2000 | Haynor et al. |
| 6,142,958 A | 11/2000 | Hammarstrom et al. |
| 6,161,032 A | 12/2000 | Acker |
| 6,173,199 B1 | 1/2001 | Gabriel |
| 6,185,448 B1 | 2/2001 | Borovsky |
| 6,186,985 B1 | 2/2001 | Snow |
| 6,190,349 B1 | 2/2001 | Ash et al. |
| 6,201,387 B1 | 3/2001 | Govari |
| 6,201,987 B1 | 3/2001 | Dumoulin |
| 6,203,493 B1 | 3/2001 | Ben-Haim |
| 6,211,666 B1 | 4/2001 | Acker |
| 6,216,026 B1 | 4/2001 | Kuhn et al. |
| 6,216,027 B1 | 4/2001 | Wills et al. |
| 6,216,028 B1 | 4/2001 | Haynor et al. |
| 6,223,066 B1 | 4/2001 | Govari |
| 6,226,547 B1 | 5/2001 | Lockhart et al. |
| 6,230,038 B1 | 5/2001 | von Gutfeld et al. |
| 6,230,042 B1 | 5/2001 | Stettenmark |
| 6,233,476 B1 | 5/2001 | Strommer et al. |
| 6,235,038 B1 | 5/2001 | Hunter et al. |
| 6,236,879 B1 | 5/2001 | Konings |
| 6,245,030 B1 | 6/2001 | DuBois et al. |
| 6,245,098 B1 | 6/2001 | Feeser et al. |
| 6,246,231 B1 | 6/2001 | Ashe |
| 6,263,230 B1 | 7/2001 | Haynor et al. |
| 6,263,260 B1 | 7/2001 | Haynor et al. |
| 6,266,551 B1 | 7/2001 | Osadohy et al. |
| 6,270,902 B1 | 8/2001 | Tedeschi et al. |
| 6,272,370 B1 | 8/2001 | Gillies et al. |
| 6,277,100 B1 | 8/2001 | Raulerson et al. |
| 6,298,257 B1 | 10/2001 | Hall et al. |
| 6,298,261 B1 | 10/2001 | Rex |
| 6,304,769 B1 | 10/2001 | Arenson et al. |
| 6,312,380 B1 | 11/2001 | Hoek et al. |
| 6,322,495 B1 | 11/2001 | Snow et al. |
| 6,322,538 B1 | 11/2001 | Elbert et al. |
| 6,329,488 B1 | 12/2001 | Terry et al. |
| 6,332,089 B1 | 12/2001 | Acker et al. |
| 6,336,906 B1 | 1/2002 | Hammarstrom |
| 6,342,120 B1 | 1/2002 | Basta |
| 6,358,197 B1 | 3/2002 | Silverman et al. |
| 6,366,799 B1 | 4/2002 | Acker et al. |

(56) References Cited

U.S. PATENT DOCUMENTS

| | | |
|---|---|---|
| 6,374,134 B1 | 4/2002 | Bladen et al. |
| 6,381,485 B1 | 4/2002 | Hunter et al. |
| 6,402,722 B1 | 6/2002 | Snow et al. |
| 6,425,853 B1 | 7/2002 | Edwards |
| 6,427,079 B1 | 7/2002 | Schneider et al. |
| 6,432,041 B1 | 8/2002 | Taniguchi et al. |
| 6,445,943 B1 | 9/2002 | Ferre et al. |
| 6,458,106 B1 | 10/2002 | Meier et al. |
| 6,461,311 B2 | 10/2002 | DuBois et al. |
| 6,471,676 B1 | 10/2002 | DeLegge et al. |
| 6,473,635 B1 | 10/2002 | Rasche |
| 6,482,170 B1 | 11/2002 | Andersen |
| 6,511,474 B1 | 1/2003 | Andersen |
| 6,517,481 B2 | 2/2003 | Hoek et al. |
| 6,551,281 B1 | 4/2003 | Raulerson et al. |
| 6,553,326 B1 | 4/2003 | Kirsch et al. |
| 6,574,498 B1 | 6/2003 | Gilboa |
| 6,579,539 B2 | 6/2003 | Lawson et al. |
| 6,582,395 B1 | 6/2003 | Burkett et al. |
| 6,596,401 B1 | 7/2003 | Terry et al. |
| 6,608,688 B1 | 8/2003 | Faul et al. |
| 6,618,612 B1 | 9/2003 | Acker et al. |
| 6,682,519 B1 | 1/2004 | Schon |
| 6,687,531 B1 | 2/2004 | Ferre et al. |
| 6,695,832 B2 | 2/2004 | Schon et al. |
| 6,702,789 B1 | 3/2004 | Owens et al. |
| 6,716,895 B1 | 4/2004 | Terry |
| 6,719,749 B1 | 4/2004 | Schweikert et al. |
| D489,452 S | 5/2004 | Schweikert |
| 6,730,096 B2 | 5/2004 | Basta |
| D491,265 S | 6/2004 | Schweikert |
| 6,749,580 B2 | 6/2004 | Work et al. |
| 6,757,557 B1 | 6/2004 | Bladen et al. |
| 6,772,002 B2 | 8/2004 | Schmidt et al. |
| 6,774,624 B2 | 8/2004 | Anderson et al. |
| 6,785,571 B2 | 8/2004 | Glossop |
| 6,786,884 B1 | 9/2004 | DeCant, Jr. et al. |
| 6,796,991 B2 | 9/2004 | Nardeo |
| 6,808,510 B1 | 10/2004 | DiFiore |
| D498,299 S | 11/2004 | Schweikert |
| 6,823,617 B2 | 11/2004 | Nardeo |
| 6,876,196 B1 | 4/2005 | Taulin et al. |
| 6,878,143 B2 | 4/2005 | Andersen |
| 6,881,211 B2 | 4/2005 | Schweikert et al. |
| D505,202 S | 5/2005 | Chesnin |
| 6,895,267 B2 | 5/2005 | Panescu et al. |
| 6,908,681 B2 | 6/2005 | Terry et al. |
| 6,911,014 B2 | 6/2005 | Wentling et al. |
| 6,916,051 B2 | 7/2005 | Fisher |
| 6,926,721 B2 | 8/2005 | Basta |
| 6,939,328 B2 | 9/2005 | Raulerson |
| 6,949,092 B1 * | 9/2005 | Moss ............................ 604/508 |
| 6,969,381 B2 | 11/2005 | Voorhees |
| 6,980,921 B2 | 12/2005 | Anderson et al. |
| 6,991,625 B1 | 1/2006 | Gately et al. |
| D515,211 S | 2/2006 | Chesnin |
| 7,015,859 B2 | 3/2006 | Anderson |
| 7,018,374 B2 | 3/2006 | Schon et al. |
| 7,096,148 B2 | 8/2006 | Anderson et al. |
| 7,158,754 B2 | 1/2007 | Anderson |
| 7,197,354 B2 | 3/2007 | Sobe |
| 2001/0045826 A1 | 11/2001 | Schneider |
| 2002/0032411 A1 | 3/2002 | Basta |
| 2002/0161306 A1 | 10/2002 | Govari |
| 2002/0161421 A1 | 10/2002 | Lee et al. |
| 2003/0066218 A1 | 4/2003 | Schweikert |
| 2003/0097099 A1 | 5/2003 | Quinn |
| 2003/0176786 A1 | 9/2003 | Maschke |
| 2004/0054350 A1 * | 3/2004 | Shaughnessy et al. ........ 604/535 |
| 2004/0087877 A1 | 5/2004 | Besz et al. |
| 2004/0087996 A1 | 5/2004 | Gambale et al. |
| 2004/0092863 A1 | 5/2004 | Raulerson et al. |
| 2004/0097903 A1 | 5/2004 | Raulerson et al. |
| 2004/0098020 A1 | 5/2004 | Nardec |
| 2004/0122416 A1 | 6/2004 | Schweikert |
| 2004/0122418 A1 | 6/2004 | Voorhees |
| 2004/0195131 A1 | 10/2004 | Spolidoro |
| 2004/0230169 A1 | 11/2004 | Felix et al. |
| 2004/0249337 A1 | 12/2004 | DiFiore |
| 2004/0249338 A1 | 12/2004 | DeCant, Jr. et al. |
| 2004/0249349 A1 | 12/2004 | Wentling |
| 2005/0000844 A1 | 1/2005 | Schweikert |
| 2005/0038453 A1 | 2/2005 | Raulerson |
| 2005/0043684 A1 | 2/2005 | Basta |
| 2005/0049572 A1 | 3/2005 | Schweikert et al. |
| 2005/0049628 A1 | 3/2005 | Schweikert et al. |
| 2005/0085765 A1 | 4/2005 | Voorhees |
| 2005/0096585 A1 | 5/2005 | Schon et al. |
| 2005/0107770 A1 | 5/2005 | Schweikert et al. |
| 2005/0120523 A1 | 6/2005 | Schweikert |
| 2005/0124970 A1 | 6/2005 | Kunin |
| 2005/0137527 A1 | 6/2005 | Kunin |
| 2005/0137580 A1 | 6/2005 | Raulerson et al. |
| 2005/0192545 A1 | 9/2005 | Voorhees et al. |
| 2005/0222593 A1 | 10/2005 | Markel et al. |
| 2005/0234369 A1 | 10/2005 | Voorhees |
| 2005/0261665 A1 | 11/2005 | Voorhees |
| 2006/0015072 A1 | 1/2006 | Raulerson |
| 2006/0015130 A1 | 1/2006 | Voorhees et al. |
| 2006/0030827 A1 | 2/2006 | Raulerson |
| 2006/0047267 A1 | 3/2006 | Gately |
| 2006/0047268 A1 | 3/2006 | Stephens |
| 2006/0064072 A1 | 3/2006 | Gately et al. |
| 2006/0173407 A1 * | 8/2006 | Shaughnessy et al. .... 604/95.01 |

FOREIGN PATENT DOCUMENTS

| | | |
|---|---|---|
| AU | 714148 | 12/1999 |
| AU | 2000PQ09592 | 8/2000 |
| AU | 2001PR05250 | 5/2001 |
| AU | 2001283703 | 5/2006 |
| CA | 1330108 | 6/1994 |
| CA | 2163622 | 12/1994 |
| CA | 2218093 | 10/1996 |
| CA | 2349724 | 5/2000 |
| CA | 2389227 | 5/2001 |
| CA | 2407461 | 3/2002 |
| CA | 2420676 | 2/2003 |
| CN | 1049288 | 2/1991 |
| CN | 1059849 | 4/1992 |
| DE | 1264317 | 3/1968 |
| DE | 2005167 | 9/1970 |
| DE | 2238722 | 2/1973 |
| DE | 2432173 | 1/1976 |
| DE | 2265373 | 9/1979 |
| DE | 2837265 | 3/1980 |
| DE | 3247548 | 7/1983 |
| DE | 3247576 | 7/1983 |
| DE | 3334174 | 9/1983 |
| DE | 3434752 | 4/1985 |
| DE | 3444807 | 6/1985 |
| DE | 3444909 | 6/1986 |
| DE | 3610270 | 11/1986 |
| DE | 8705894 | 6/1987 |
| DE | 3611112 | 7/1987 |
| DE | 3645161 | 3/1992 |
| DE | 3884020 | 3/1994 |
| DE | 69102293 | 10/1994 |
| DE | 68918888 | 3/1995 |
| DE | 69209707 | 10/1996 |
| DE | 69216468 | 5/1997 |
| DE | 69216513 | 5/1997 |
| DE | 3752245 | 2/1999 |
| DE | 19830183 | 7/1999 |
| DE | 69425034 | 3/2001 |
| DE | 68918632 | 10/2003 |
| DE | 69332716 | 10/2003 |
| DE | 69730135 | 7/2005 |
| DE | 69733010 | 2/2006 |
| EP | 0091577 | 10/1983 |
| EP | 0102342 | 3/1984 |
| EP | 0125843 | 11/1984 |
| EP | 0125844 | 11/1984 |
| EP | 0160395 | 11/1985 |

(56) References Cited

FOREIGN PATENT DOCUMENTS

| | | |
|---|---|---|
| EP | 0182539 | 5/1986 |
| EP | 0242051 | 10/1987 |
| EP | 0256546 | 2/1988 |
| EP | 0259945 | 3/1988 |
| EP | 0263645 | 4/1988 |
| EP | 0274412 | 7/1988 |
| EP | 0282143 | 9/1988 |
| EP | 0307162 | 3/1989 |
| EP | 0320623 | 6/1989 |
| EP | 0347035 | 12/1989 |
| EP | 0355996 | 2/1990 |
| EP | 0357397 | 3/1990 |
| EP | 0359697 | 3/1990 |
| EP | 0382974 | 8/1990 |
| EP | 0399536 | 11/1990 |
| EP | 0421650 | 4/1991 |
| EP | 0440427 | 8/1991 |
| EP | 0454293 | 10/1991 |
| EP | 0456342 | 11/1991 |
| EP | 0476807 | 3/1992 |
| EP | 0502664 | 9/1992 |
| EP | 0513991 | 11/1992 |
| EP | 0537136 | 4/1993 |
| EP | 0773810 | 5/1997 |
| EP | 0839547 | 5/1998 |
| EP | 0846959 | 6/1998 |
| EP | 1036570 | 9/2000 |
| EP | 1310514 | 5/2003 |
| EP | 1313527 | 5/2003 |
| EP | 1477202 | 11/2004 |
| EP | 1913926 | 4/2008 |
| FR | 0565491 | 1/1924 |
| FR | 0591963 | 7/1925 |
| FR | 0900765 | 7/1945 |
| FR | 1511044 | 1/1968 |
| FR | 2276483 | 1/1976 |
| GB | 745379 | 2/1956 |
| GB | 891754 | 3/1962 |
| GB | 2067574 | 7/1981 |
| JP | 58170869 | 10/1983 |
| JP | 1104250 | 4/1989 |
| JP | 3051052 | 3/1991 |
| JP | 4092668 | 3/1992 |
| JP | 4224766 | 8/1992 |
| JP | 5245209 | 9/1993 |
| NZ | 234127 | 10/1992 |
| WO | WO 8800810 | 2/1988 |
| WO | WO 8905671 | 6/1989 |
| WO | WO 9002514 | 3/1990 |
| WO | WO 9003777 | 4/1990 |
| WO | WO 9101772 | 2/1991 |
| WO | WO 9203090 | 3/1992 |
| WO | WO 9304628 | 3/1993 |
| WO | WO 9311823 | 6/1993 |
| WO | WO 9406636 | 3/1994 |
| WO | WO 9421318 | 9/1994 |
| WO | WO 9428953 | 12/1994 |
| WO | WO 9605768 | 2/1996 |
| WO | WO 9607352 | 3/1996 |
| WO | WO 9632060 | 10/1996 |
| WO | WO 9729683 | 8/1997 |
| WO | WO 9818515 | 5/1998 |
| WO | WO 9944668 | 9/1999 |
| WO | WO 0012165 | 3/2000 |
| WO | WO 0038567 | 7/2000 |
| WO | WO 0060996 | 10/2000 |
| WO | WO 0174434 | 10/2001 |
| WO | WO 0189603 | 11/2001 |
| WO | 02/15973 A1 | 2/2002 |
| WO | WO 0213899 | 2/2002 |
| WO | WO 0215973 | 2/2002 |
| WO | WO 0218004 | 3/2002 |
| WO | WO 03043679 | 5/2003 |
| WO | WO 03047636 | 6/2003 |
| WO | WO 2004041329 | 5/2004 |
| WO | WO 2004060437 | 7/2004 |
| WO | WO 2004075962 | 9/2004 |
| WO | WO 2004087249 | 10/2004 |
| WO | WO 2005035040 | 4/2005 |
| WO | WO 2005065761 | 7/2005 |
| WO | 2006/076214 A2 | 7/2006 |

OTHER PUBLICATIONS

Gauderer et al., "Gastrostomy Without Laparotomy: A Percutaneous Endoscopic Technique", Journal of Pediatric Surgery, vol. 15, No. 6 (Dec. 1980), pp. 872-875.
"A Simplified Technique for Constructing a Tube Feeding Gastrostomy", Gauderer and Ponsky, Reprint from Surgery, Gynecology & Obstetrics, Jan. 1981, vol. 152, pp. 82-85.
Enteral Systems Brochure, Corpak, Inc., Aug. 1982.
Flexiflo-III Enteral Nutrition Pump Operating Manual, Ross Laboratories, 1985 on or before December thereof.
Corpak's Proven Enteral Delivery System—Complete and Versatile, advertisement, Corpak Company, 1986 on or before December thereof.
KM-80 Enteral Feeding Pump Operating Instructions, O'Brien, available prior to 1986 on or before December thereof.
Shike et al., "Percutaneous Endoscopic Jejunostomy in Cancer Patients With Previous Gastric Resection", Gastrintestinal Endoscopy, vol. 33, No. 5, 1987, pp. 372-374.
Corpak Enternal Feeding Pump Model VTR 300, Corpak, Inc., 1987 on or before December thereof.
Wu et al., "New Method of Percutaneous Gastrostomy Using Anchoring Devices", America Journal of Surgery, Am J. Surg 1987; 153: pp. 230-232, Feb. 1987.
Flow Through Stylet Connector, Corpak MedSystems, Aug. 19, 1987.
Flexiflo® Companion® Enteral Nutrition Pump Operating Manual, Ross Laboratories, 1987 on or before December thereof.
Corpak Enternal Feeding Pump Model 300 D, Corpak, Inc., 1989 on or before December thereof.
Starkhammar et al., "Cath-FInder™ Catheter Tracking System: a new device for positioning of central venous catheters. Early experience from implantation of brachia portal systems," Acta Anaesthesiol Scand, 1990 on or before December thereof, pp. 296-300.
Shike et al., "Direct Percutaneous Endoscopic Jejunostomies", Gastrointestinal Endoscopy, vol. 37, No. 1, 1991, pp. 62-65.
"Direct Percutaneous Endoscopic Jejunostomy", Blair S. Lewis, MD, Gastrointestinal Endoscopy, vol. 37, No. 4, 1991, p. 493.
kangaroo® 324 Feeding Pump Operating Manual, Sherwood Medical Company, 1991 on or before December thereof.
"Corscope Endoscopically Placed Feeding Tube" brochure, copyright 1992, on or before December thereof.
Flexiflo® Quantum™ Enteral Pump Operating Manual, Ross Laboratories, 1992 on or before December thereof.
"Silk Over-the-Wire Jejunostomy Tube" brochure, copyright 1993, on or before December thereof.
Etzkorn et al., "A New Technique for Jejunal Feeding Tube Placement: A Marriage of Enterscope and Laparoscope," Gastrointestinal Endoscopy, vol. 43, No. 6, 1996, pp. 610-613.
Central Venous Catheter Placement Using Electromagnetic Position Sensing: A Clinical Evaluation, by Hans Starkhammar, MD, PhD, Mats Bengtsson, MD, PhD, Donald A. Kay and Alan R. Shapiro, Mar./Apr. 1996, pp. 164-170.
Williams et al., "Luminal Devices, the Cathlocator: A novel non-radiological method for the localization of enteral tubes", Journal of Gastroenterology and Hepatology (1996) 11, pp. 500-505, date 1996 on or before December of such year.
Borkowski, "Pediatric Surgery for the Primary Care Pediatrician, Part II" from Pediatric Clinics of North America, vol. 45, No. 6, Dec. 1998.
The Farrell Valve Enteral Gastric Pressure Relief System Advertisement, 1999 in or before the month of December thereof.
Department of Health and Human Services, Navi-Star Diagnostic/Ablation Deflectable Tip Catheter, Food and Drug Administration, Jun. 15, 2000.

(56) References Cited

OTHER PUBLICATIONS

Daniels et al., "Recurrent Sigmoid Volvulus Treated by Percutaneous Endoscopic Colostomy", British Journal of Surgery in the year 2000 in or before the month of December thereof.
Young et al., "A Novel Technique for Nasoduodenal Feeding Tube Placement in Critically Ill Patients", dated Feb. 14, 2002.
Heriot et al., "The Application of Percutaneous Endoscopic colostomy to the Management of Obstructed Defecation", from the Department of Colorectal Surgery, St. Richard's Hospital, Chichester, England, May 2002.
Extender cable graphic, manufactured by LEMO USA Inc., distributed and sold by HLC Ltd. as of Jul. 29, 2002.
Olympus Medical Endoscope & Surgical Products, Olympus, printed from http://www.olympus.co.jp/LineUP/Endoscope/indexE.html, Oct. 17, 2002.
CF-Q160AL innoflex™, Olympus® Focus on Life, printed from http://www.olympusamerica.com/msg_section, Oct. 22, 2002.
CF-Q160S, EVIS EXERA™, Olympus® Focus on Life, printed from http://www.olympusamerica.com/msg_section, Oct. 22, 2002.
EVIS 140 Series, printed from http://www.olympus.co.jp, Oct. 22, 2002.
EVIS 240 Series, printed from http://www.olympus.co.jp, Oct. 22, 2002.
GIF-N30 Fiberscope, Olympus® focus on Live, printed from http://www.olympusamerica.com/msg_section, Oct. 22, 2002.
GIF-XP160, SlimSIGHT™, Olympus® Focus on Life, printed from http://www.olympusamerica.com/msg_section, Oct. 22, 2002.
Multiple Lesion™ FFR of Serial Tandem Lesions, Florence Medical, printed from http://www.florencemedical.com, Oct. 22, 2002.
Olympus Medical Endoscope & Surgical Products, Olympus, printed from http://www.olympus.co.jp/en/mesg/endoscope, Oct. 22, 2002.
SmartFlow® Family of Product, Simultaneous CFR/FFR™, printed from http://www.florencemedical.com/aboutFlorence/history.htm, Oct. 22, 2002.
Biosense Webster, A Johnson & Johnson Company, CARTO™ EP Navigation System, printed from http://www.biosensewebster.com/US/products_carton av.htm, Oct. 23, 2002.
Biosense Webster, A Johnson & Johnson Company, CUSOMCATH™ Program, printed from http://www.biosensewebster.com/US/products.htm, Oct. 23, 2002.
Lucent® Medical Systems, Adding Intelligence to Indwelling devices, printed from http://www.lucentmedical.com/overview2.htm., Oct. 23, 2002.
Lucent® Medical Systems, Enteral Feeding Tubes, printed from http://www.lucentmedical.com/et.htm, Oct. 23, 2002.
Lucent® Medical Systems, The LMS—Zortran™ printed from http://www.lucenmedical.com/zortran.htm, Oct. 23, 2002.
News from NAVION™ printed from http://www.navionbiomedical.com/system.htm, Oct. 23, 2002.
Research in Catheter and Tube Placement, printed from http://www.navionbiomedical.com/system.htm, Oct. 23, 2002.
The NAVION™ BioNavigation System, printed from http://www.navionbiomedical.com/system.htm, Oct. 23, 2002.
Cathlocator™ "Implementing new standards in patient care with products that incorporate the Cathlocator™ system" from www.micronix.com printed on Oct. 25, 2002.
Navi-Star® diagnostic/Ablation Deflectable Tip Catheter, U.S. Food and Drug Administration—Center for Devices and Radiological health, printed in 2002, on or before the month of December thereof.
Buehrle, "PICC Placement in Humans Using Electromagnetic Detection," TVAP Inc. Durham NC, 2002 on or before December thereof.
Enbohm et al. "Radio-Frequency Interface—An EMC Study of the Cathlocator™," Institute of Technology, Department of Biomedical Engineering, Master's Thesis, Dec. 20, 2002.
New and Emerging Techniques—Surgical, Rapid Review, Percutaneous Endoscopic Sigmoid Colostomy, Australian Safety and Efficacy Register of New Interventional Procedures—Surgical, Jun. 2003.
"Newsletter, new products update", published by Medicina prior to Jul. 2004.
Medicina™ Extension Feeding Set photograph, prior to Jul. 2004.
Medicina™ Feeding Syringe photograph, prior to Jul. 2004.
Medicina™ Feeding Tube photograph, prior to Jul. 2004.
1P Series Catalog, prior to Jan. 13, 2005.
FMN Connector Connectors for FFC, written by JST, pp. 390-391, prior to Jan. 13, 2005.
LEMO's Push-Pull Self-Latching Connection System, p. 5, LEMO USA Inc., prior to Jan. 13, 2005.
Selection of contact types, p. 9, LEMO USA Inc., prior to Jan. 13, 2005.
Children's Medical Ventures Extension Set for Feeding Tube photograph, prior to Sep. 7, 2005.
Children's Medical Ventures Feeding Tube photograph, prior to Sep. 7, 2005.
Exacta-Med® Dispenser photograph, prior to Sep. 7, 2005.
IV Line photograph, prior to Sep. 7, 2005.
IV Syringe photograph, prior to Sep. 7, 2005.
VIASYS MedSystems™ Neonatal/Pediatric Feeding Tube photograph, prior to Sep. 7, 2005.
International Search Report dated Sep. 22, 2008, for corresponding Intl. Appln. No. PCT//US06/00381.
Canadian Office Action dated Oct. 9, 2009, for corresponding Canadian Appln. No. 2,594,734.
Chinese Office Action mailed May 28, 2010, for corresponding Chinese Appln. No. 200680006456.2.
European Search Report dated Sep. 17, 2009, for corresponding European Appln. No. 06717560.4.
European Search Report mailed Nov. 3, 2010, for corresponding European Appln. No. 10008275.9.

\* cited by examiner

APPARATUS AND METHOD USED WITH GUIDANCE SYSTEM FOR FEEDING AND SUCTIONING

BACKGROUND

Physicians and other health care providers frequently use catheters to treat patients. Catheters include a tube which is inserted into the human body. Certain catheters are inserted into through the patient's nose or mouth for treating the gastrointestinal tract. These catheters, sometimes referred to as enteral catheters, typically include feeding tubes. The feeding tube lies in the stomach or intestines, and a feeding bag delivers liquid nutrient, liquid medicine or a combination of the two to the patient. When a feeding tube is inserted though a patients nare, and it is determined that a patient cannot be fed into the stomach, a second tube is typically inserted through the patient's other nare.

When using catheters, it is important to place the end of the catheter at the proper location within the human body. Erroneous placement of the catheter tip may injure or harm the patient. For example, if the health care provider erroneously places an enteral catheter into the patient's lungs, liquid may be introduced into the lungs with harmful results. If the health care provider erroneously places a catheter into the wrong cavity of the cardiovascular system, the patient may experience infection or a harmful blockage.

In some cases, health care providers use X-ray machines to gather information about the location of the catheters within the body. There are several of disadvantages with using X-ray machines. For example, X-rays from these machines are a known carcinogen, if received in sufficient doses. Also, X-ray machines are relatively large and heavy, consume a relatively large amount of energy and may expose the patient to a relatively high degree of radiation. Also, these machines are typically not readily accessible for use because, due to their size, they are usually installed in a special X-ray room. This room can be relatively far away from the patient's room. Therefore, health care providers can find it inconvenient to use these machines for their catheter procedures. Furthermore, it can be inconvenient to transport these machines to a patient's home for home care catheter procedures.

Accordingly, there is a need to overcome each of these disadvantages.

SUMMARY

In one example embodiment, the tube assembly is configured to allow: (a) enteral feeding; and (b) gastric suctioning or decompression. In one example embodiment, the tube assembly is configured to be used in conjunction with a tube assembly guidance system. In one example embodiment, the tube assembly includes a first connector and a feeding tube having: (a) a first end connected to the first connector; and (b) a second end configured to allow enteral feeding. In one example embodiment, the feeding tube has a first length from the first end to the second end. In example embodiment, the tube assembly includes a second connector connected to the feeding tube. In one example embodiment, the tube assembly includes a suctioning tube configured to receive the feeding tube. In one example embodiment, the suctioning tube has: (a) a third end connected to the second connector; and (b) a portion configured to be placed through a patient's nare. In one example embodiment, the portion includes a fourth end configured to allow suctioning or decompression of the patients stomach. In one example embodiment, the suctioning tube has a second length from the third end to the fourth end. In one example embodiment, the first length is greater than the second length by at least a distance from the patient's stomach to the patient's jejunum such that the second end of the feeding tube is configured to be released and advanced into the patient's jejunum to allow enteral feeding into the jejunum while the fourth end of the suctioning tube remains positioned in the patient's stomach.

In one example embodiment, the tube assembly includes a magnetic field generator.

In one example embodiment, the second end and the fourth end are configured to be simultaneously advanced into the patient's stomach.

In one example embodiment, after the second end and the fourth end are placed into the patient's stomach: (a) feeding can be achieved using the feeding tube; and (b) suctioning can be achieved using the tube.

In one example embodiment, the second connector is releaseably connected to the feeding tube such that, after the second end the fourth end are placed into the patient's stomach, the second end is configured to be advanced from the patient's stomach into a small bowel of the patient while the fourth end remains in the patient's stomach.

In one example embodiment, the tube assembly includes a sleeve configured to secure the third end to the second connector.

In one example embodiment, the tube assembly includes a plug configured to stabilize a position of the feeding tube relative to the suctioning tube.

In one example embodiment, the first connector includes a first y-port connector, and the second connector includes a second y-port connector.

In one example embodiment, a method of tracking a first end of a feeding tube and a second end of a suctioning tube which in configured to receive the feeding tube includes: (a) causing a processor to execute instructions to operate with a display device to display a reference image; (b) causing the processor to execute the instructions to, using a magnetic field generator, operate with the display device to display a first position of the first end and the second end; and (c) thereafter, causing the processor to execute the instructions to operate with the display device to display a second position of the first end, the second position being different from the first position based on the first end being advanced into a lower intestine of the patient, the second end remaining at the first position.

The tube assembly disclosed herein thus is used with only one nare of the patient and is for both feeding and suctioning. If gastric feeding is not tolerated by the patient's stomach, the feeding tube can be advanced into the small bowel of the patient with the aid of a tube assembly guidance system, thereby eliminating the need to transport the patient to a Radiology Unit or Gastroenterology Unit. Advancing the feeding tube and suctioning tube at the bedside reduces therapy downtime, x-ray exposure and costly procedures practiced in Radiology or Gastroenterology.

Additional features and advantages are described herein, and will be apparent from the following Detailed Description and figures.

DETAILED DESCRIPTION

Figure 1:
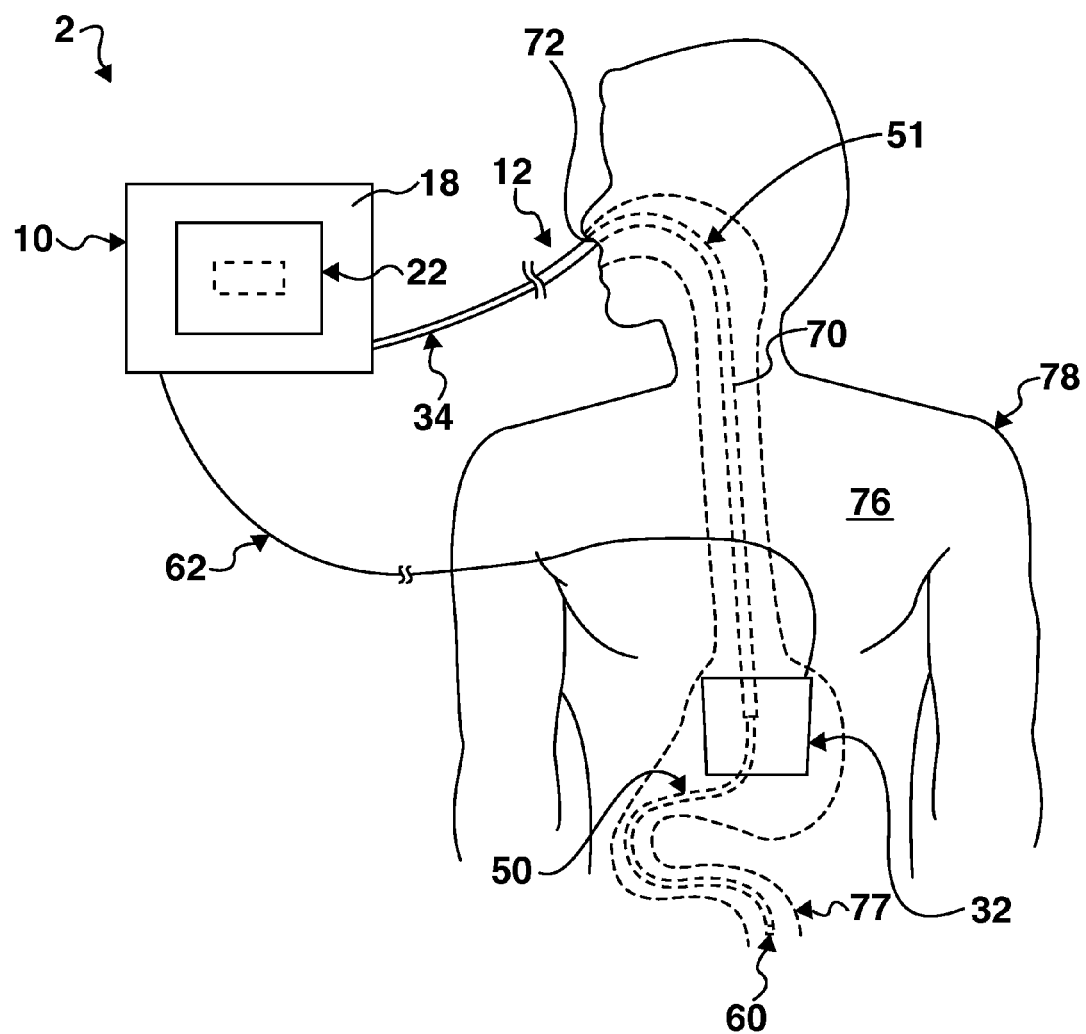
FIG. 1 is a top or plan view of one example embodiment of the catheter unit and the display device, illustrating an enteral application involving a portion of the tubing assembly inserted into a human body and indication of catheter information on the display device.
Figure 2:
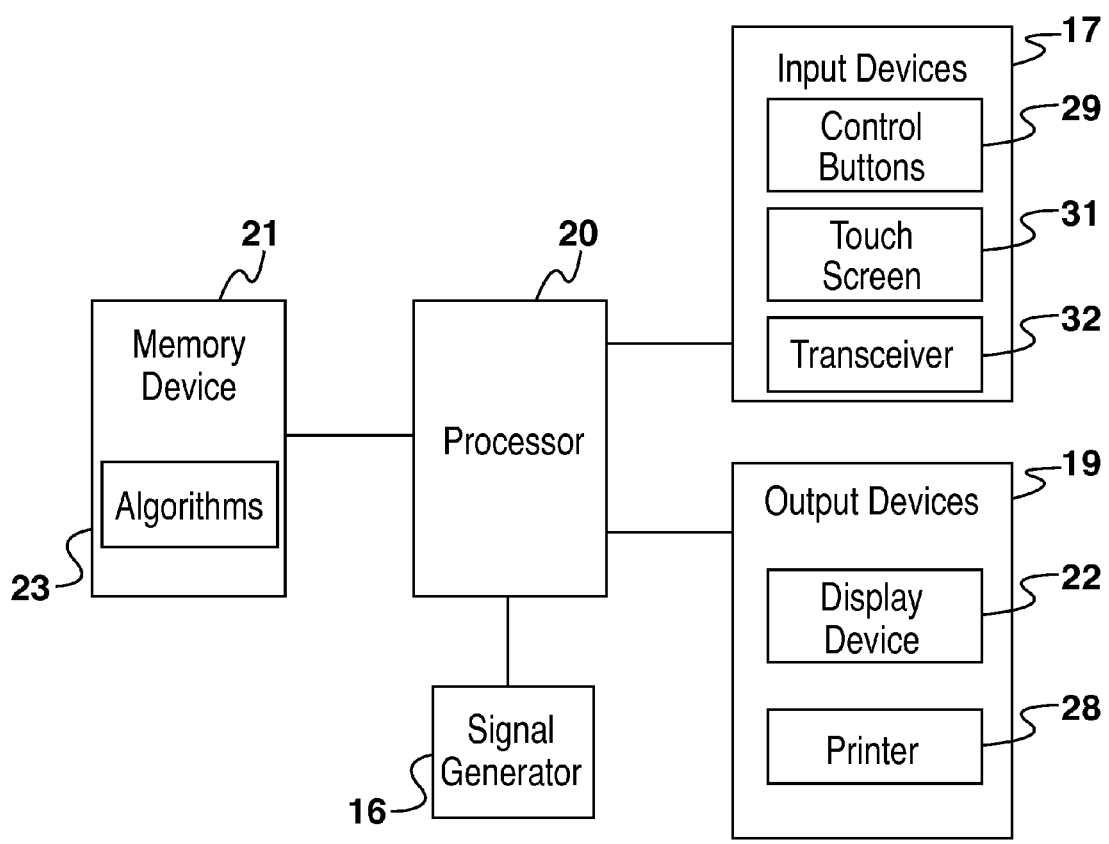
FIG. 2 is schematic block diagram of one example embodiment of the electronic configuration of the catheter position guidance system, illustrating the processor, memory device, signal generator, input devices and output devices.

FIGS. 1 and 2 depict a catheter position guidance system not unlike that described in U.S. Pat. No. 7,976,518. That patent is hereby incorporated into this specification by reference. Where a definition or use of a term in U.S. Pat. No. 7,976,518 is inconsistent or contrary to the definition of that term provided herein, the definition of that term provided herein applies and the definition of that term in the reference does not apply.

This invention also relates to a method of catheter location in a human body not unlike that described in U.S. Patent Publication No. 2010/0097373. That patent publication is hereby incorporated into this specification by reference. Where a definition or use of a term in U.S. Patent Publication No. 2010/0097373 is inconsistent or contrary to the definition of that term provided herein, the definition of that term provided herein applies and the definition of that term in the reference does not apply.

Referring now to the drawings, in one example illustrated in FIGS. 1 and 2, the catheter position guidance system or catheter guidance system 2 includes: (a) an apparatus 10 having a housing 18 which supports a controller or processor 20 and a display device 22; (b) a non-invasive movable receiver-transmitter or transceiver 32 electronically coupled to the processor 20 by a wire, cable, signal data connection or signal carrier 62; and (c) an invasive catheter unit 12 in communication with the transceiver 32 and operatively coupled to the apparatus 10 by a wire, cable, chord or electrical extension 34, which, in turn, is operatively coupled to the processor 20. It should be appreciated that the transceiver 32 can include a device which has a separate signal receiver and signal transmitter. The transceiver 32 can also include a single device which functions so as to receive and transmit signals.

As best illustrated in FIG. 2, the system, in one example embodiment, includes: (a) a plurality of input devices 17 for providing input signals to the system 2 such as one or more control buttons 29, a touch screen 31 and the transceiver 32; (b) a signal generating assembly 16 which produces or generates electronic signals that are received by the transceiver 32; (c) a memory device 21 including machine readable instructions and one or more computer programs (which, for example, may include a plurality of algorithms 23) which are used by the processor 20 to process the signal data produced by the signal generating assembly 16 and transmitted by the transceiver 32; and (d) a plurality of output devices 19 such as the display device 22 and the printer 28 which indicate the catheter information to the health care provider. The display device 22 may be any suitable display mechanism including, but not limited to, a liquid crystal display (LCD), light-emitting diode (LED) display, cathode-ray tube display (CRT) or plasma screen.

Health care providers can use the system 2 in a variety of catheter applications. In one example illustrated in FIG. 1, the system 2 is used in an enteral application. Here, a portion 70 of the catheter unit 12 is placed through the patient's nose 72. The distal end or tip 60 of the catheter unit 12 is positioned in the lower intestine, more specifically, in the patient's jejunum 77. Here, the end of the suctioning tube 51 remains positioned in the patient's stomach 74. The health care provider places the transceiver 32 over the chest area 76 of a body 78. The display device 22 and the printer 28 indicate information related to the location of the portion 70 of the catheter unit 12 within the body 78, as well as information related to the shape of the pathway taken by the catheter unit 12. It should be appreciated that the system 2 need not indicate the exact location or path of the catheter unit 12 to provide assistance to the health care provider.

Figure 3:
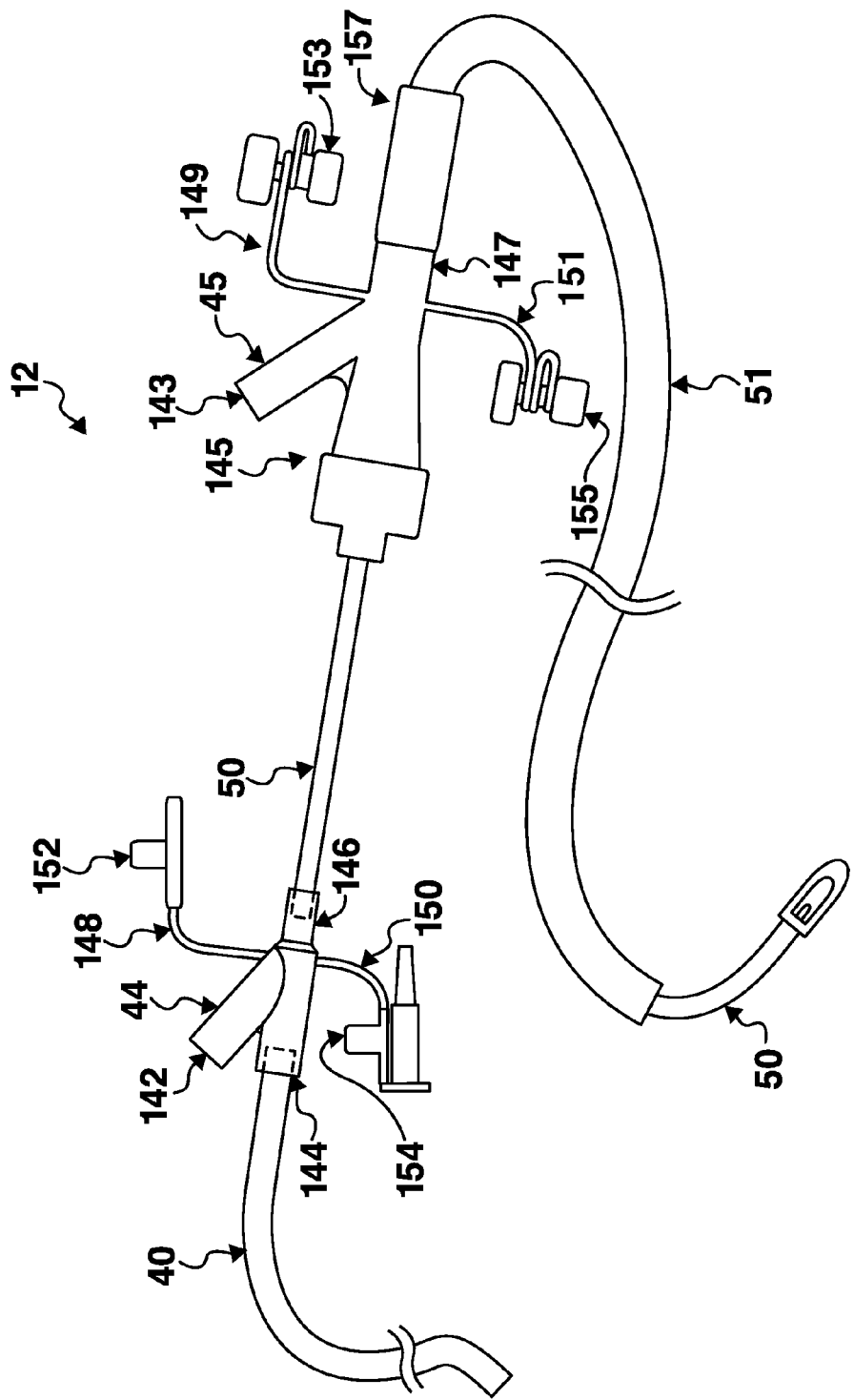
FIG. 3 is a perspective view of one example embodiment of the catheter unit, illustrating the tubing assembly and the signal generator being received by and housed in the tubing assembly.
Figure 4:
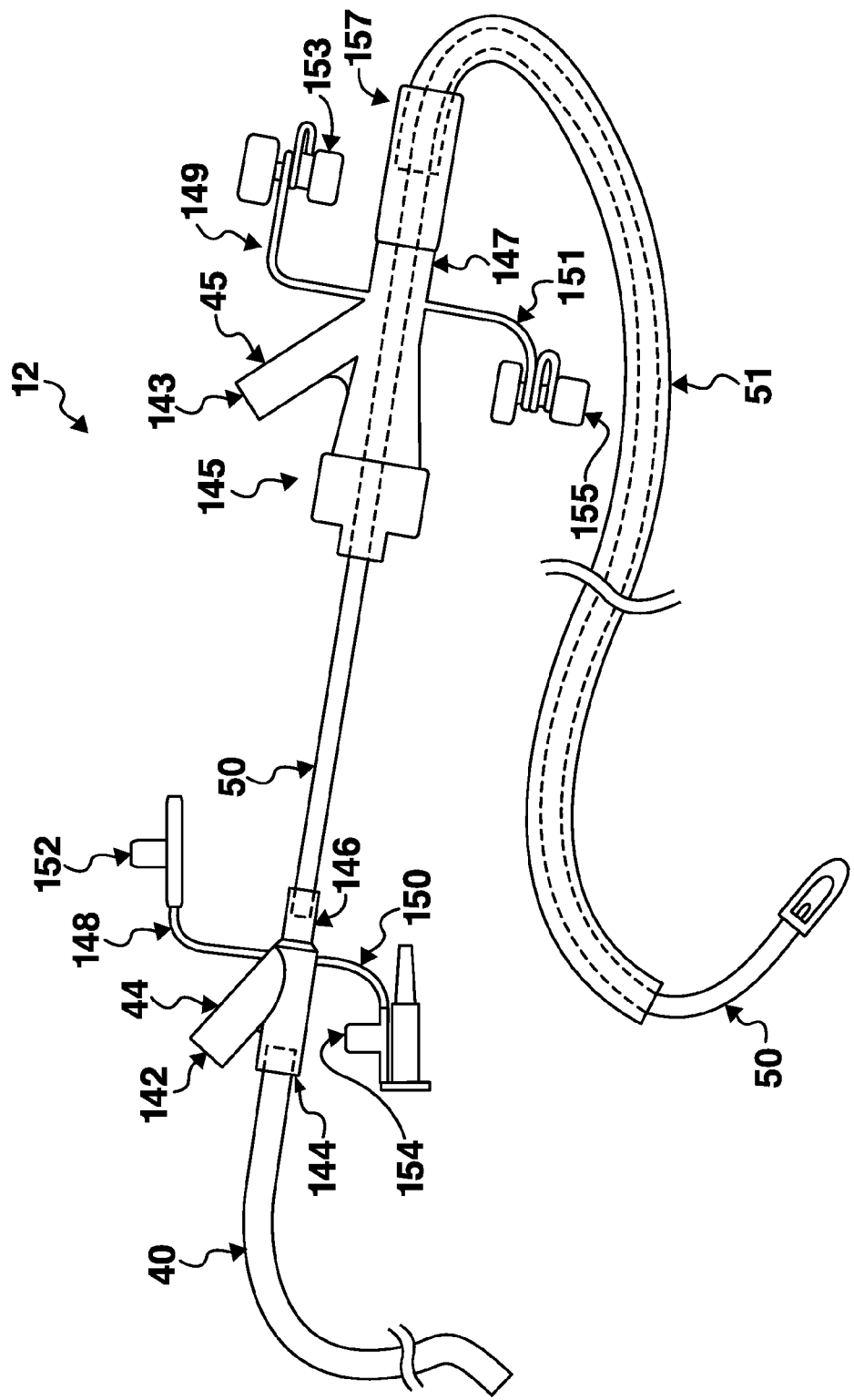
FIG. 4 is a perspective view of one example embodiment of the tubing assembly, illustrating the suctioning tube receiving the feeding tube.
Figure 5:
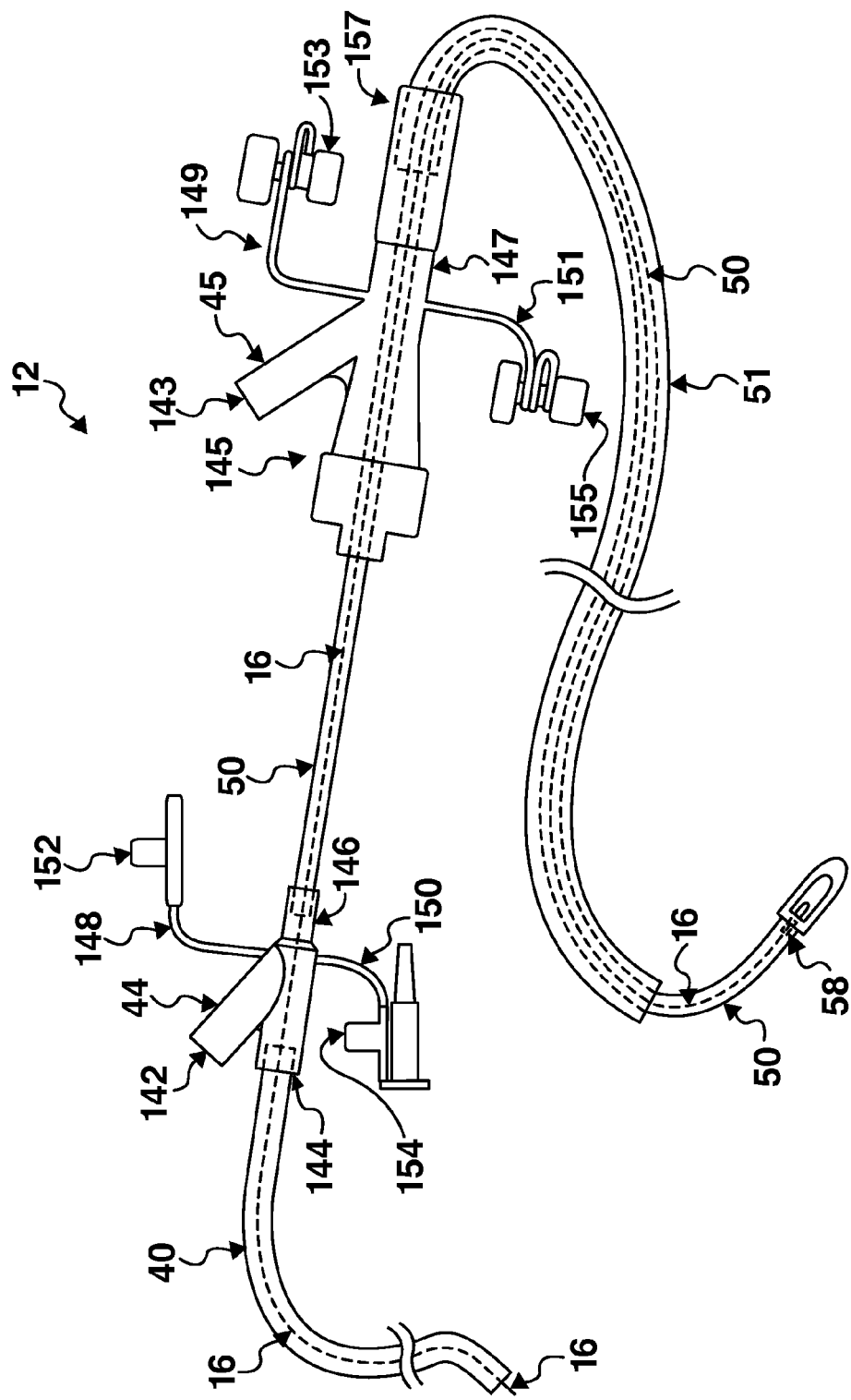
FIG. 5 is a perspective view of one example embodiment of the catheter unit showing, illustrating the tubing assembly and the signal generating assembly.

Referring to FIGS. 3 to 5, in one example embodiment, the catheter unit 12 includes a tubing assembly 14 which receives and houses the signal generating assembly 16.

In one example embodiment, the tubing assembly 14 includes: (a) a tube or an electrical tubular insulator 40; (b) a first connector such as a multi-port connector or y-port connector 44 attachable to the tubular insulator 40; (c) a second tube such as a catheter or a feeding tube 50, connected to the y-port connector 44; (d) a second connector such a second multi-port connector or second y-port connector 45, connected to the feeding tube 50; a third tube such a second catheter or a suctioning tube 51; and (e) a feeding tube end, bolus or tip 60 attached to the distal end of the feeding tube 50.

In one example embodiment, the multi-port or y-port connector 44 includes: (a) a liquid delivery branch, medicine delivery branch or medicine branch 142 for distributing drugs, medicine or other medicinal liquids to the patient; (b) a nutrient delivery branch or feeding branch 144 sized to receive the insert 124 of the tubular insulator 40; (c) a catheter or feeding tube connection branch 146 attached to the feeding tube 50; (d) a flexible or movable arm 148; and (e) a flexible or moveable arm 150. In an alternative embodiment, y-port connector 44 includes additional branches for administering various nutrients or medicines to the body 78. In another alternative embodiment, the y-port connector 44 includes only a feeding branch 144 and a connection branch 146. The arm 148 has a stopper 152, and the arm 150 has a stopper 154. The stoppers 152 and 154 are sized to prevent fluid from passing through the branches 142 and 144 after such branches 142 and 144 are plugged with stoppers 152 and 154, respectively. In addition, the arm 150 includes a fastener which secures a tube-size adapter to the arm 150. The tube-size adapter enables fluid delivery tubes (not shown) having various diameters to connect to the feeding branch 144 of the y-port connector 44.

In one example embodiment, the feeding tube 50 includes: (a) a proximal end attached to the catheter connection branch 146 of the y-port connector 44; (b) a distal end; and (c) an external surface. The proximal end is insertable into the feeding tube connection branch 146 of the y-port connector 44 so as to bring the feeding tube 50 into fluid communication with the y-port connector 44. In one embodiment, the external surface has a plurality of volumetric, measurement or unit markings uniformly spaced along the body of the feeding tube. These markings assist the user in measuring the flow or distribution of liquid to or from the patient. In an alternative embodiment, markings function as placement markers which assist the user in assessing the depth that the feeding catheter is placed within the human body.

In one example embodiment, the end member, bolus or tip 60 is attached to the distal end of the feeding tube 50. The tip 60 includes a body having a collar and an end member. The body defines a passage and an opening. The opening is positioned between the collar and the end member. A portion of the end member can have a rounded shape. The shape of the passage and opening of the tip 60 is configured to facilitate the flow of fluid from the feeding tube 50 into the patient's body while decreasing the likelihood that the opening will become clogged.

In one example embodiment, the second multi-port or y-port connector 45 includes: (a) a suctioning branch 143 which can be used for suctioning to check gastric residuals; (b) a suctioning branch 145 sized to receive the feeding tube 50; (c) a second catheter or suctioning tube connection branch 147 attached to the suctioning tube 51; (d) a flexible or movable arm 149; and (e) a flexible or moveable arm 151. The arm 149 has a stopper 153, and the arm 151 has a stopper 155. The stoppers 153 and 155 are sized to prevent air and/or fluid from passing through the branches 145 and 147 after such branches 145 and 147 are plugged with stoppers 153 and 155, respectively.

In one example embodiment, the tubing assembly includes a plug which is configured to be inserted into the second nutrient delivery branch 145. In this example embodiment the plug is configured to stabilize a position of the feeding tube relative to second multi-port connector and thus also the suctioning tube.

In one example embodiment, the suctioning tube 51 includes: (a) a proximal end attached to the suctioning tube connection branch 147 of the y-port connector 45; (b) a distal end; and (c) an external surface. The proximal end is insertable into the catheter connection branch 147 of the y-port connector 45 so as to bring the suctioning tube 51 into fluid communication with the y-port connector 45. In one embodiment, the external surface has a plurality of volumetric, measurement or unit markings uniformly spaced along the body of the suctioning tube. In one example embodiment, markings function as placement markers which assist the user in assessing the depth that the suctioning tube is placed within the human body.

In one example embodiment, the tubing assembly includes a sleeve 157 which is configured to help secure the suctioning tube 51 to the second connector 45.

The tubular connector 40, y-port connector 44, y-port connector 45, feeding tube 50 and suctioning tube 51 can be made from any suitable polymer or plastic material including, but not limited to, polyamide, polyethylene, polypropylene, polyurethane, silicone and polyacrylonitrile.

In one example embodiment, the invasive signal generating assembly 16 includes a magnetic energy generator or magnetic field generator 58 operatively coupled to the distal end of a wire assembly 38. The tubular insulator 40 described above covers a portion of the wire assembly 38.

In operation, when the apparatus 10 sends electrical current to coils of the magnetic field generator 58, and the coils transmit a signal or electromagnetic field capable of being detected by the non-invasive transceiver 32. The transceiver 32 detects the electromagnetic field or signal generated by the magnetic field generator 58 inside the human body. The processor 20 causes the display device 22 and the printer 28 to produce graphics which assist the health care provider in the catheter placement procedure.

In one example embodiment, the method of tracking the placement of the generator 58 includes first step of determining the length of the feeding tube 50 and the suctioning tube 51. Next, prior to placing the suctioning tube 51 into the human body for suctioning and the feeding tube 50 into the human body for enteral feeding, the user or assembler places the magnetic field generator 58 at a desired location within the feeding tube 50.

Figure 6A:
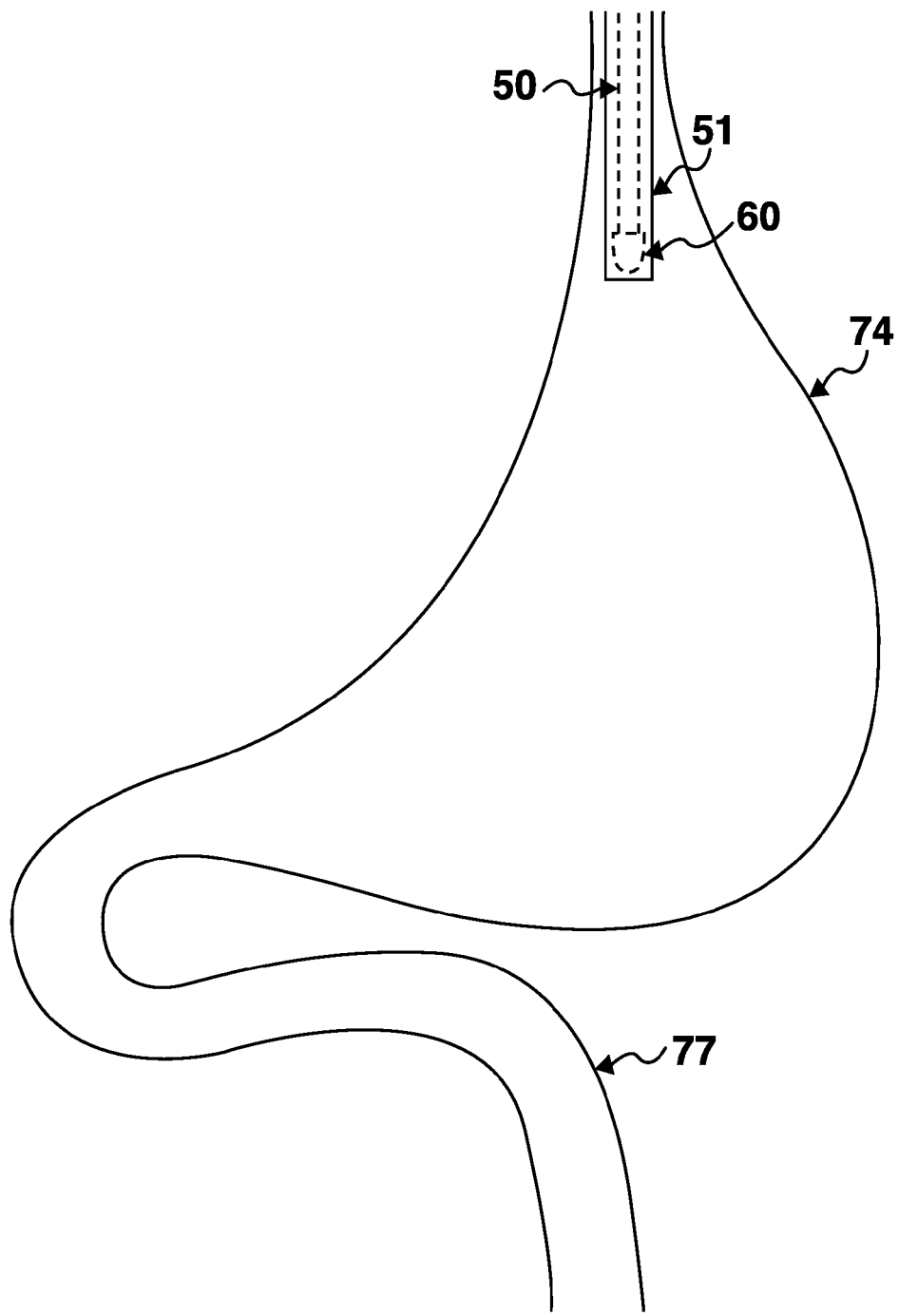
FIGS. 6A, 6B and 6C are top or plan views of one example embodiment of certain portions of the tube assembly, illustrating an end of the feeding tube being advanced to the patient's small bowel after the end of the feeding tube and the end of the suctioning tube have been placed in the patient's stomach.

Once the position of the generator 58 has been properly set, the health care provider places the transceiver 32 on the patient's chest and inserts the suctioning tube 51 and the feeding tube 50 into the patient's stomach through a patient's nare. While doing so, the display device 22 displays graphics 37 that help the user in guiding the end of the suctioning tube 51 and the end of the feeding tube 50 to a desired location within the human body. Once the end of the suctioning tube 51 and the end of the feeding tube 50 are placed in the desired location, the user can remove the signal generating assembly 16 while the position of the suctioning tube 51 and the feeding tube 50 is maintained as shown in FIG. 6A. The user then attaches medicine and nutritional delivery tubes to the y-port connector 44 for introducing fluids into the body for medical treatment.

Figure 6B:
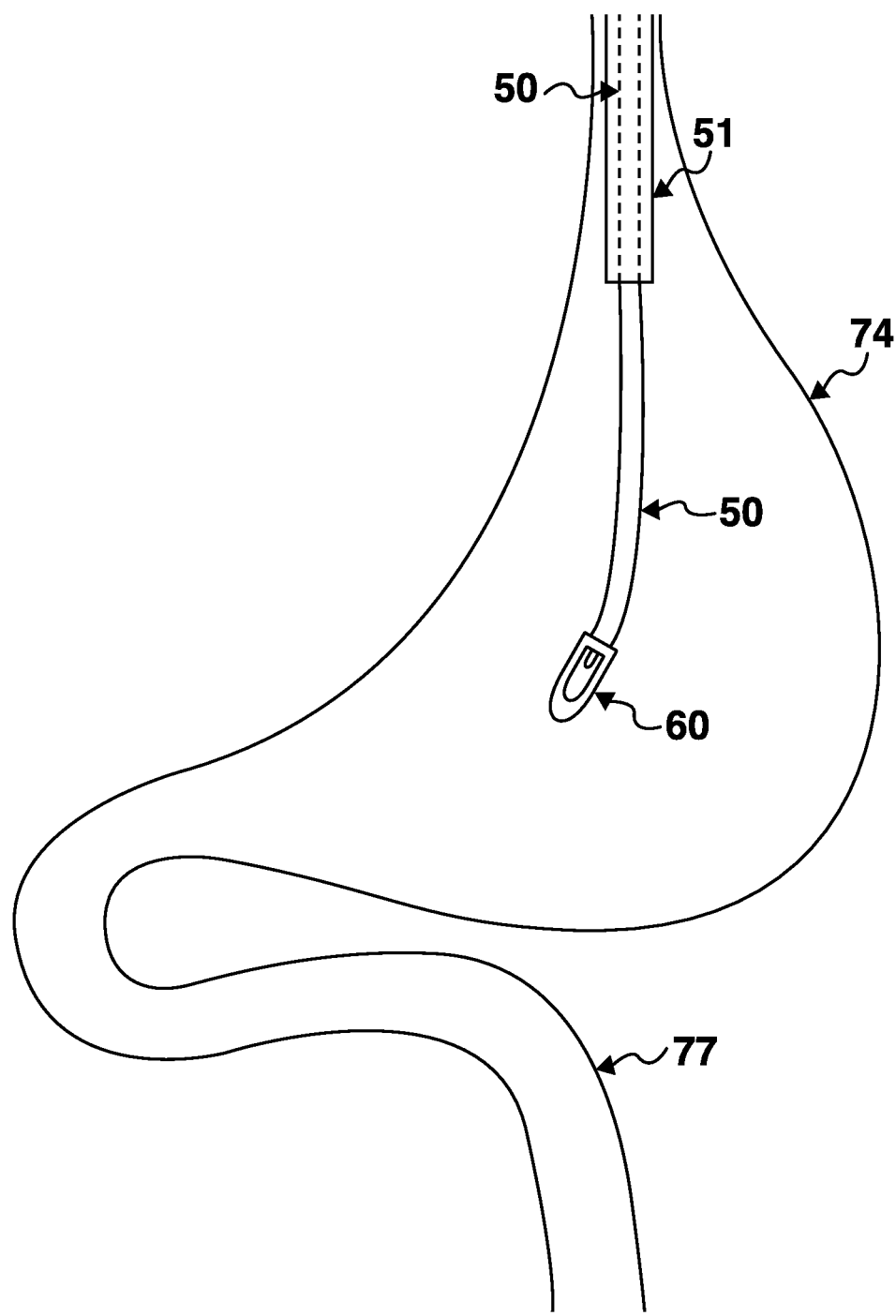
Figure 6C:
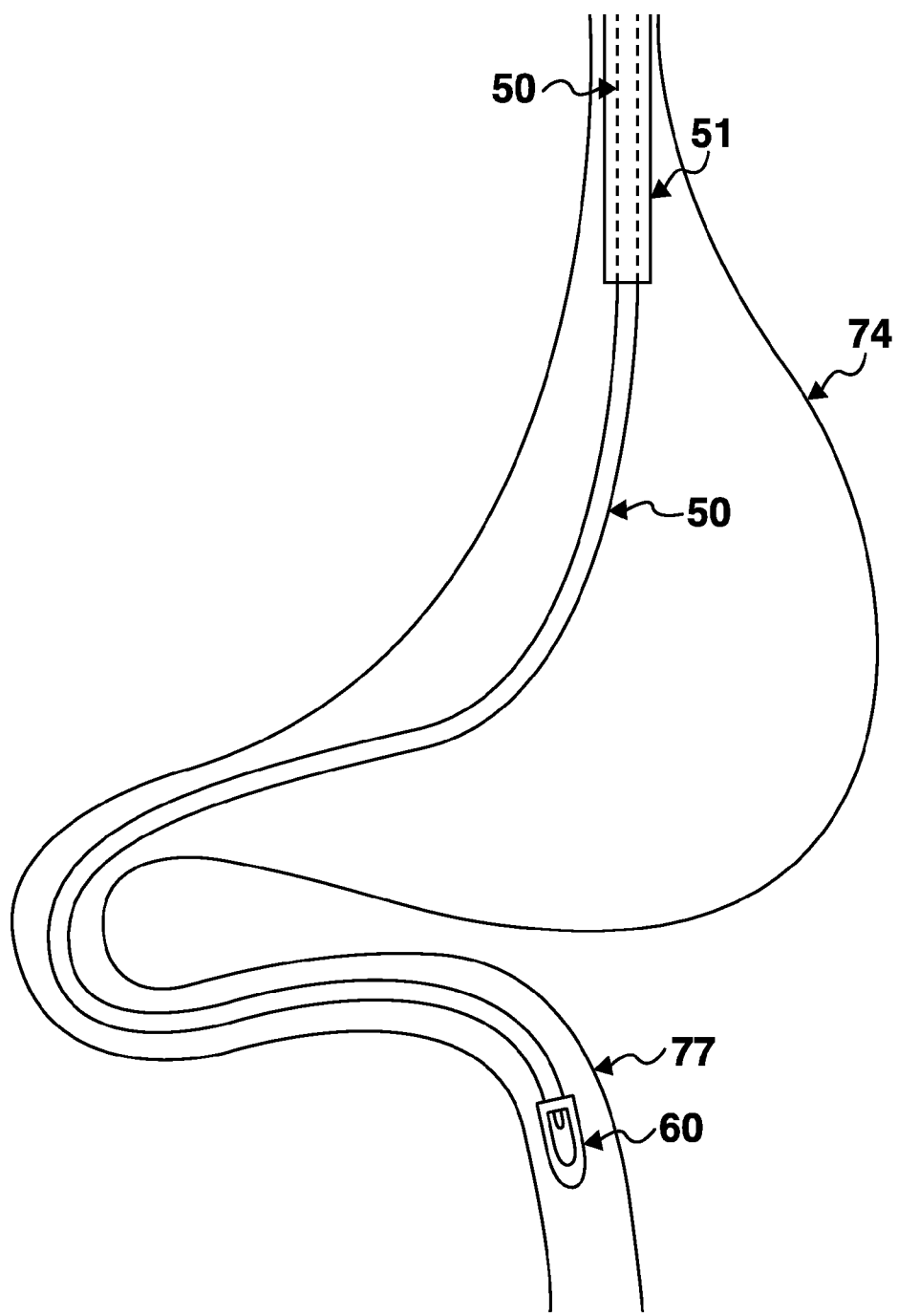

Thereafter, if it is determined that the stomach cannot handle feeding, the signal generating assembly is reinserted into the feeding tube 50, and the end of the feeding tube 50 is advanced into the small bowel of the patient as shown in FIGS. 6B and 6C. While doing so, the display device 22 displays graphics 37 that help the user in guiding the end of the feeding tube 50 to a desired location within the human body. Once the end of the feeding tube 50 is placed in the desired location, the user removes the signal generating assembly 16 while the position of the suctioning tube 51 and the feeding tube 50 is maintained. The user can then reattach the medicine and nutritional delivery tubes to the y-port connector 44 for introducing fluids into the body for medical treatment. In this example embodiment, as the end of the feeding tube is advanced to the patient's small bowel, the end of the suctioning tube 51 remains in the patient's stomach to allow suctioning and decompression as shown in FIGS. 6B and 6C.

It should also be appreciated that these procedures may involve treatment of humans by physicians, physician assistants, nurses or other health care providers. In addition, these procedures may involve treatment of other mammals and animals by veterinarians, researchers and others.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A tube assembly for: (a) enteral feeding; and (b) gastric suctioning or decompression, the tube assembly configured to be used in conjunction with a tube assembly guidance system, the tube assembly comprising:
    a first connector;
    a feeding tube having:
    (a) a first end connected to the first connector; and
    (b) a second end configured to allow enteral feeding, wherein the feeding tube has a first length from the first end to the second end;
    a second connector connected to the feeding tube;
    a suctioning tube configured to receive the feeding tube, the suctioning tube having:
    (a) a third end connected to the second connector; and (b) a portion configured to be placed through a patients nare, the portion including a fourth end configured to advance only into the patient's stomach, such that the fourth end remains inside the patient's stomach, to allow suctioning or decompression of the patients stomach, wherein the suctioning tube has a second length from the third end to the fourth end, wherein, when the second end of the feeding tube and the fourth end of the suctioning tube are positioned in the stomach, the second end of the feeding tube is configured to allow enteral feeding into the stomach, and the second connector is releaseably connected to the feeding tube, and wherein the first length is greater than the second length by at least a distance from the patient's stomach to the patient's jejunum such that the second end of the feeding tube is configured to be released and advanced into the patient's jejunum to allow enteral feeding into the jejunum while the fourth end of the suctioning tube remains positioned in the patient's stomach.

2. The tube assembly of claim 1, which includes a magnetic field generator.

3. The tube assembly of claim 1, wherein the second end and the fourth end are configured to be simultaneously advanced into the patient's stomach.

4. The tube assembly of claim 1, which includes a sleeve configured to secure the third end to the second connector.

5. The tube assembly of claim 1, wherein:
(a) the first connector includes a first y-port connector; and
(b) the second connector includes a second y-port connector.

* * * * *